US006790669B1

(12) United States Patent
Pfeiffer et al.

(10) Patent No.: US 6,790,669 B1
(45) Date of Patent: Sep. 14, 2004

(54) METHOD FOR CHEMICAL ANALYSIS OF BIOLOGICAL MATERIAL

(75) Inventors: Curtis D. Pfeiffer, Midland, MI (US); Nile N. Frawley, Midland, MI (US); Thomas L. Peters, Midland, MI (US); Philip J. Savickas, Midland, MI (US); David R. Albers, Midland, MI (US); Steven J. Gluck, Lake Jackson, TX (US); Lawrence W. Nicholson, Freeland, MI (US); Jose B. Esquivel H., Midland, MI (US)

(73) Assignee: The Dow Chemical Company, Midland, MI (US)

( * ) Notice: Subject to any disclaimer, the term of this patent is extended or adjusted under 35 U.S.C. 154(b) by 86 days.

(21) Appl. No.: 10/018,629

(22) PCT Filed: Jul. 13, 2000

(86) PCT No.: PCT/US00/19418

§ 371 (c)(1),
(2), (4) Date: Dec. 14, 2001

(87) PCT Pub. No.: WO01/04622

PCT Pub. Date: Jan. 18, 2001

Related U.S. Application Data

(60) Provisional application No. 60/143,533, filed on Jul. 13, 1999.

(51) Int. Cl.[7] .............................................. G01N 30/14
(52) U.S. Cl. ......................... 436/161; 436/63; 436/71; 436/86; 436/94; 436/174; 436/178
(58) Field of Search ................................. 436/161, 174, 436/178, 63, 71, 86, 94

(56) References Cited

U.S. PATENT DOCUMENTS 5,589,619 A * 12/1996 Chappell et al. ............ 800/278

6,544,566 B1 * 4/2003 Waggle et al. .............. 424/757

OTHER PUBLICATIONS

Derwent Acc. No. 1994–107916. Abstract of SU 1790895A, Kipriyanova et al. "Determination of Vitamin A in biological material by extraction with aqueous solution of isopropanol and liquid chromatography . . . ".*

* cited by examiner

Primary Examiner—Jan M. Ludlow

(57) ABSTRACT

A chemical analysis method for determining chemically related differences between subject biological material such as genetically modified plant material and control biological material such as genetically unmodified plant material, which method includes at least the following six steps. The first step is to contact the subject biological material with a fluid extractant, such as a mixture of water, isopropanol and potassium hydroxide, to produce a fluid extract of the subject biological material. The second step is to contact the control biological material with the fluid extractant to produce a fluid extract of the control biological material. The third step is to chromatograph the fluid extract of the subject biological material, for example, gas or fluid chromatography, to produce a chromatogram of the fluid extract of the subject biological material. The fourth step is to chromatograph the fluid extract of the control biological material to produce a chromatogram of the fluid extract of the control biological material. The fifth step is to determine the differences between the chromatograms, for example, by using the method of U.S. Pat. No. 5,592,402, to identify at least one outlier peak. The sixth step is to determine the chemical identity of the outlier peak, for example, using gas chromatography/mass spectroscopy analysis of the outlier peak.

9 Claims, 24 Drawing Sheets

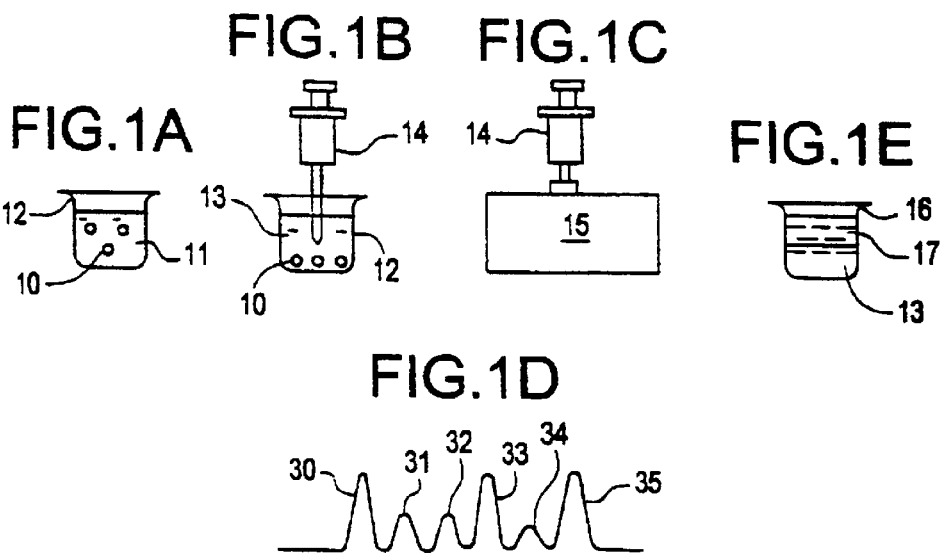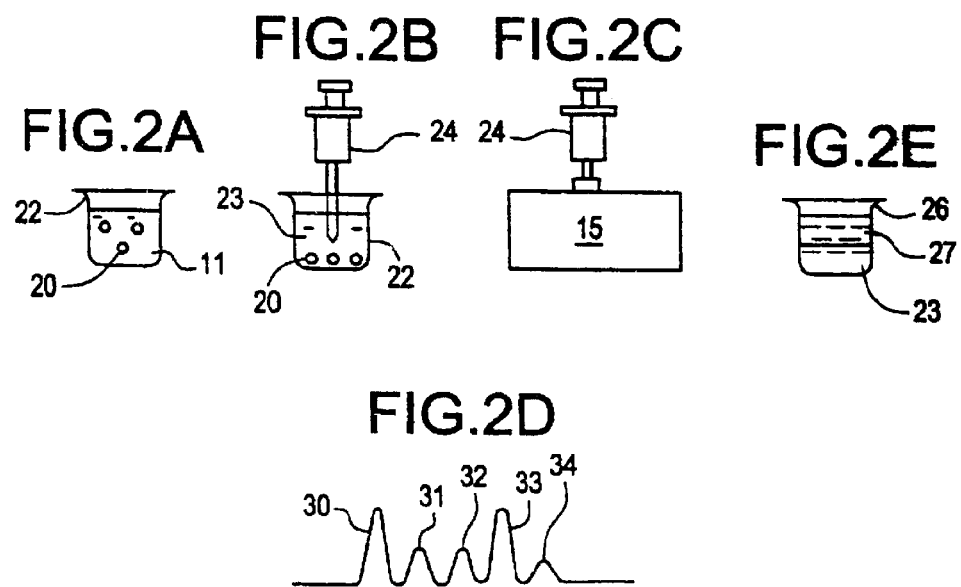

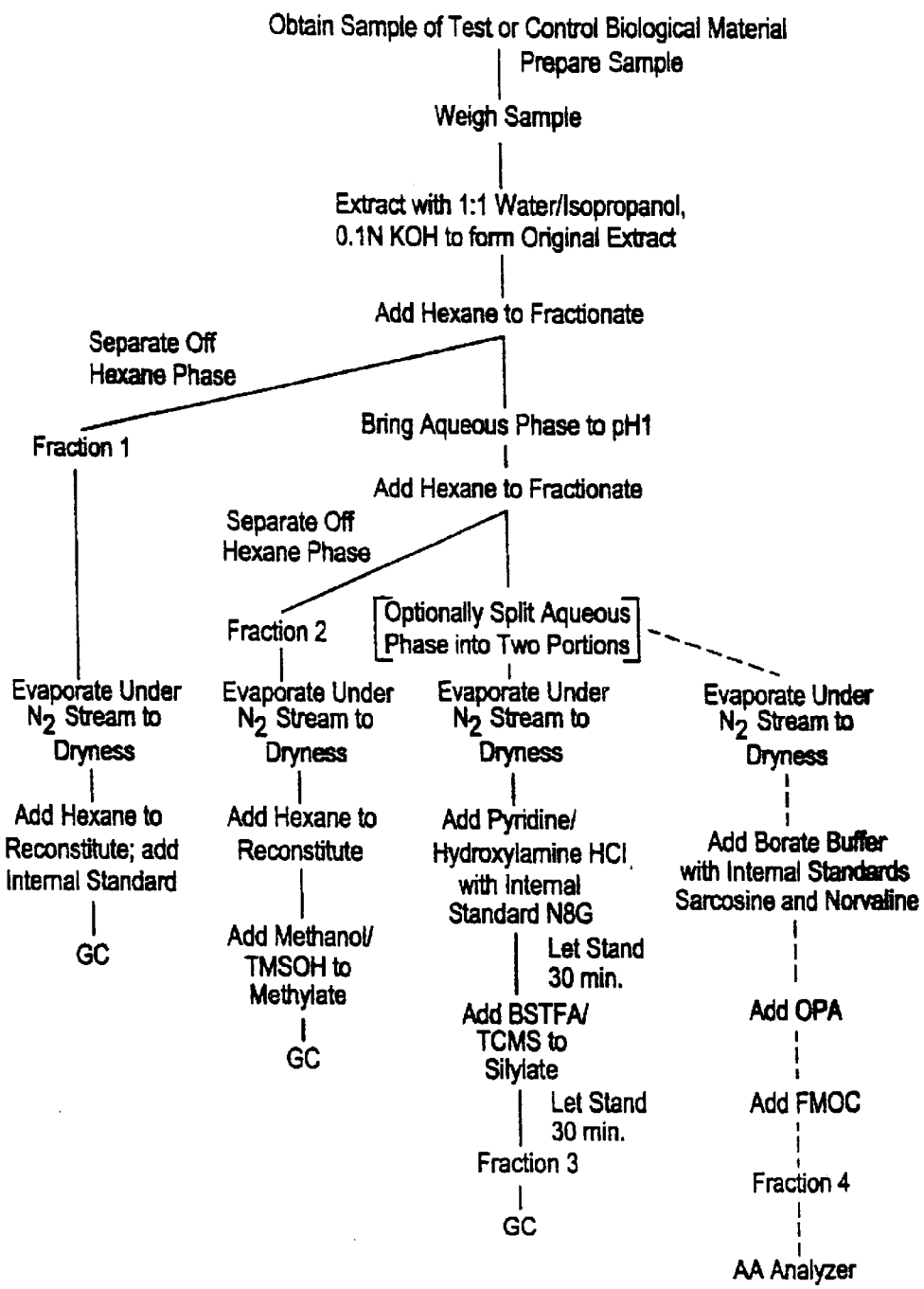

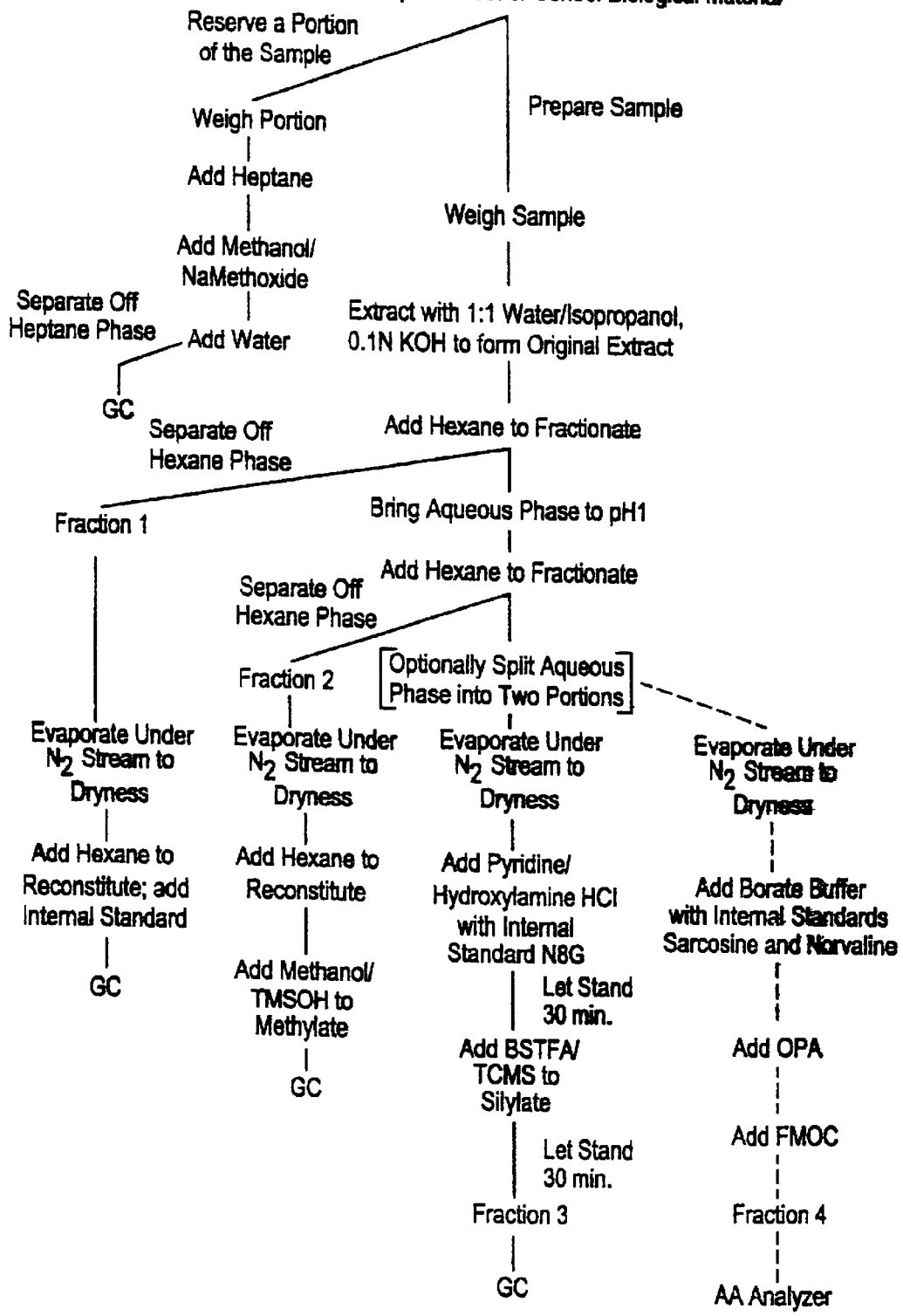

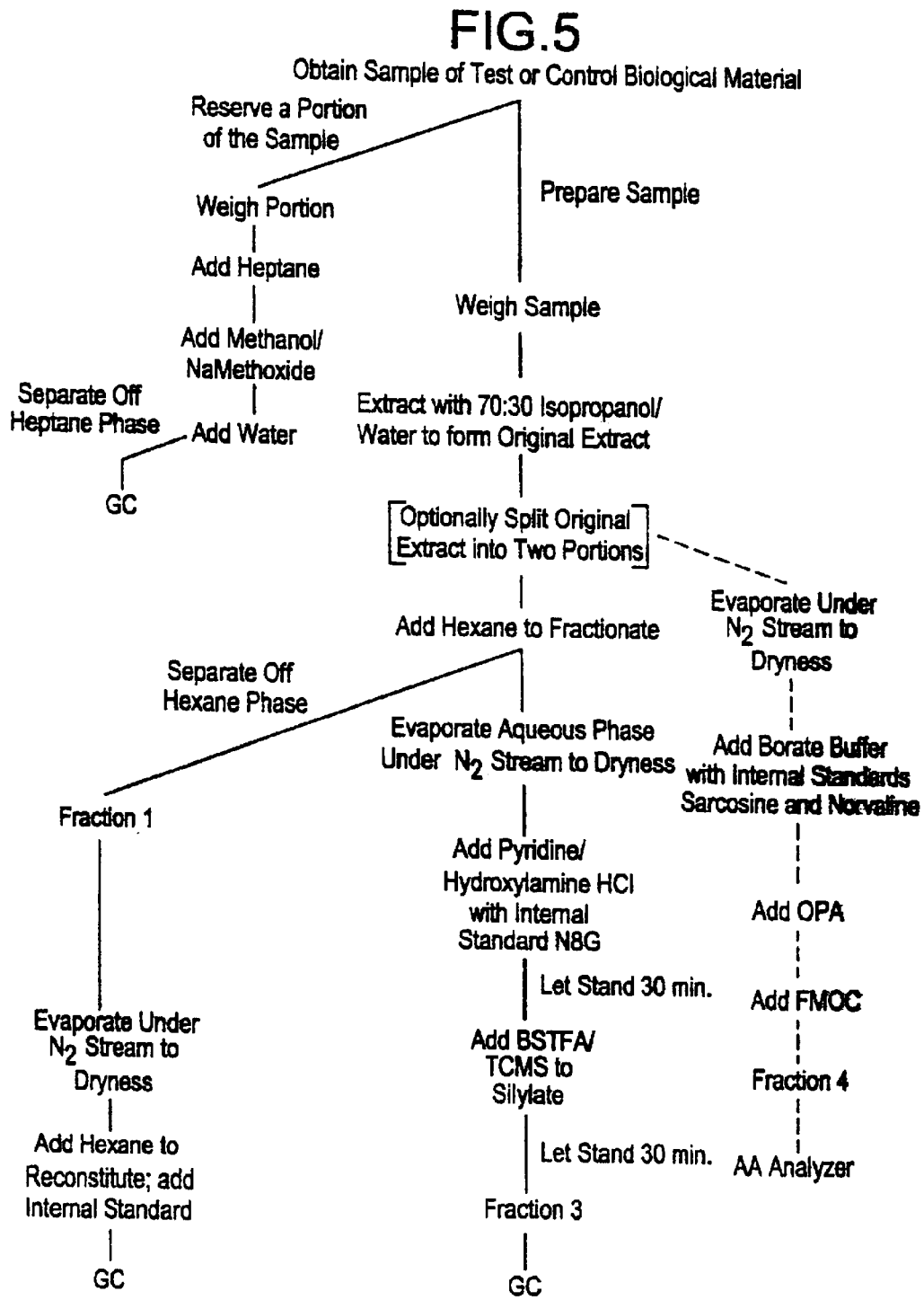

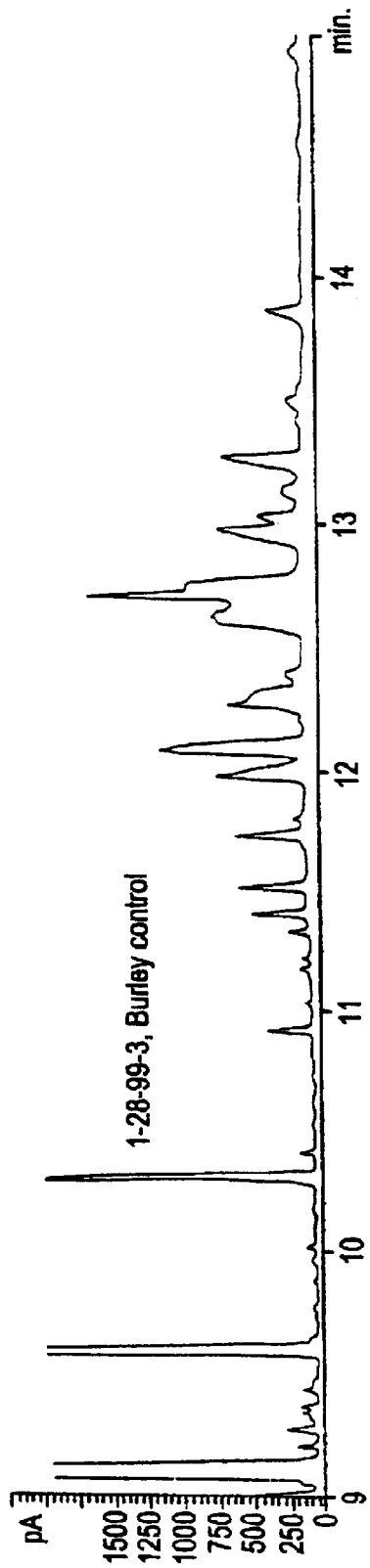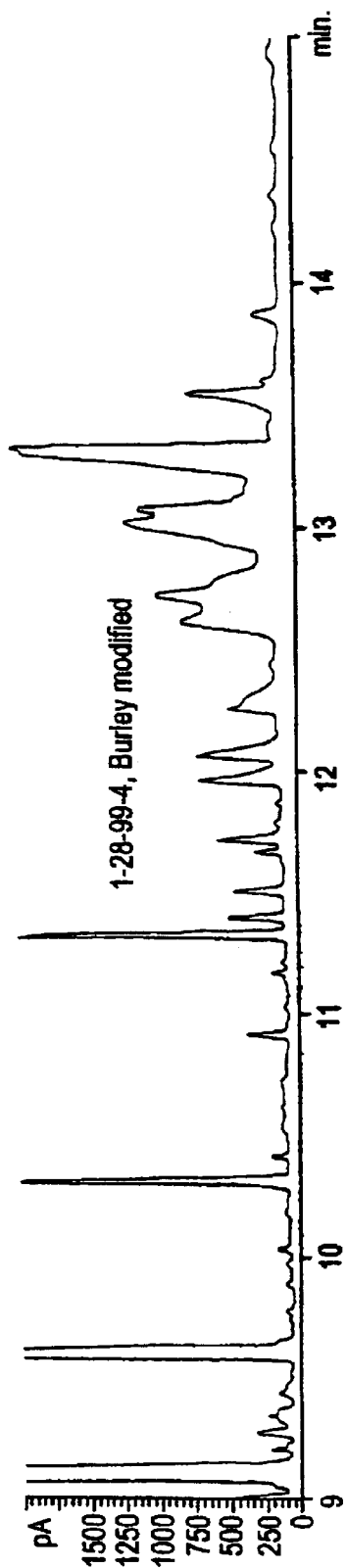

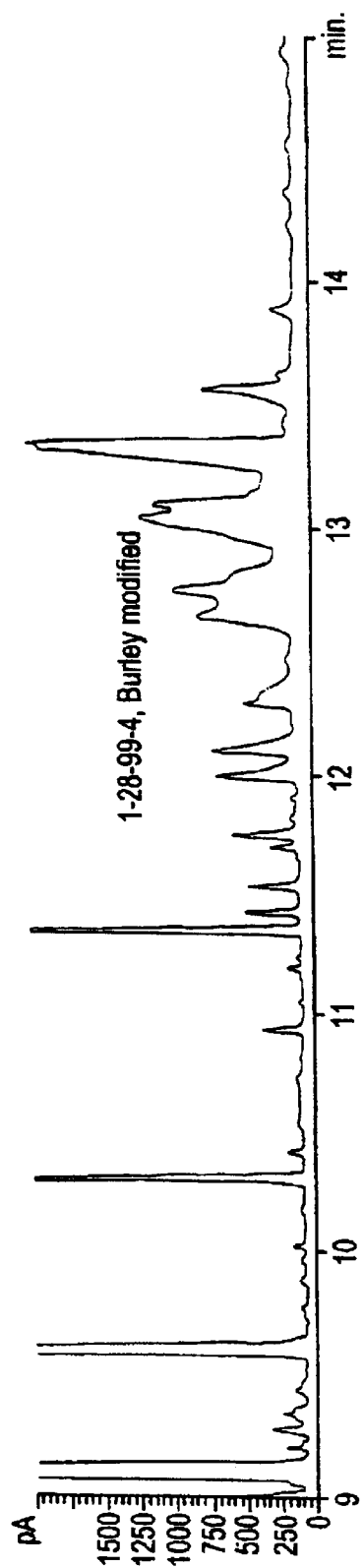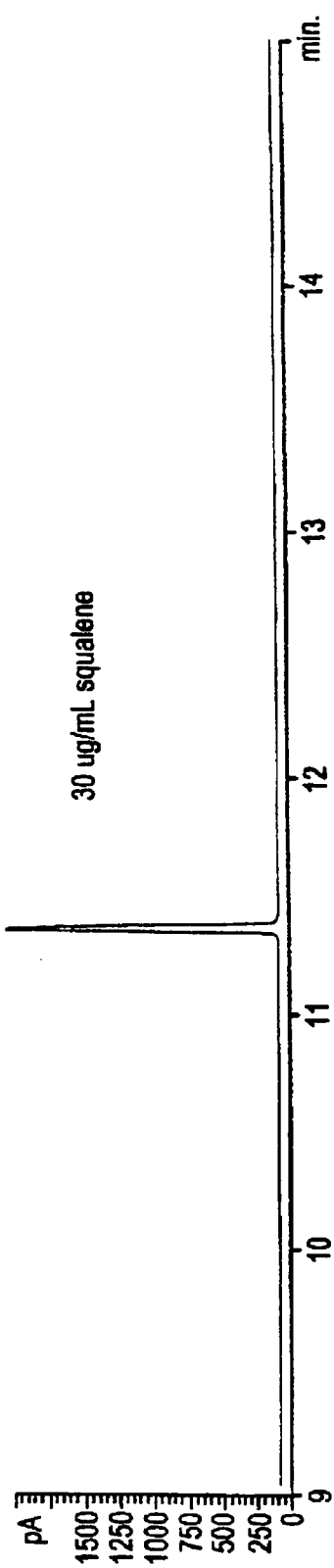

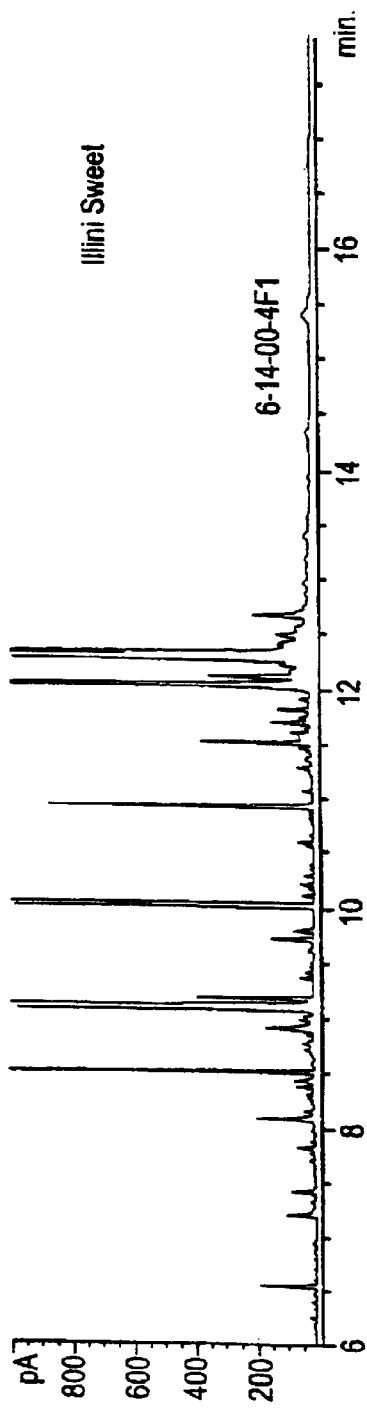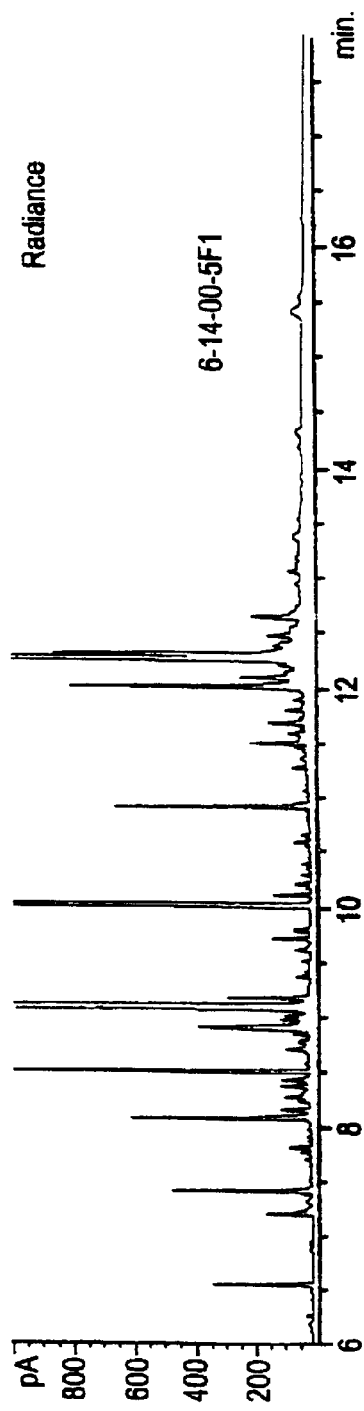

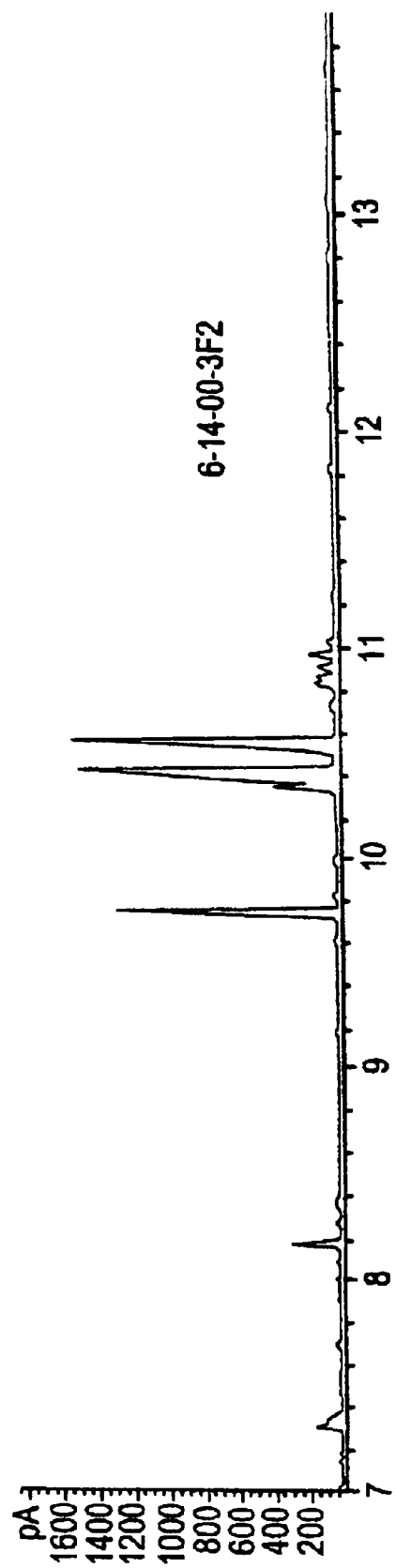

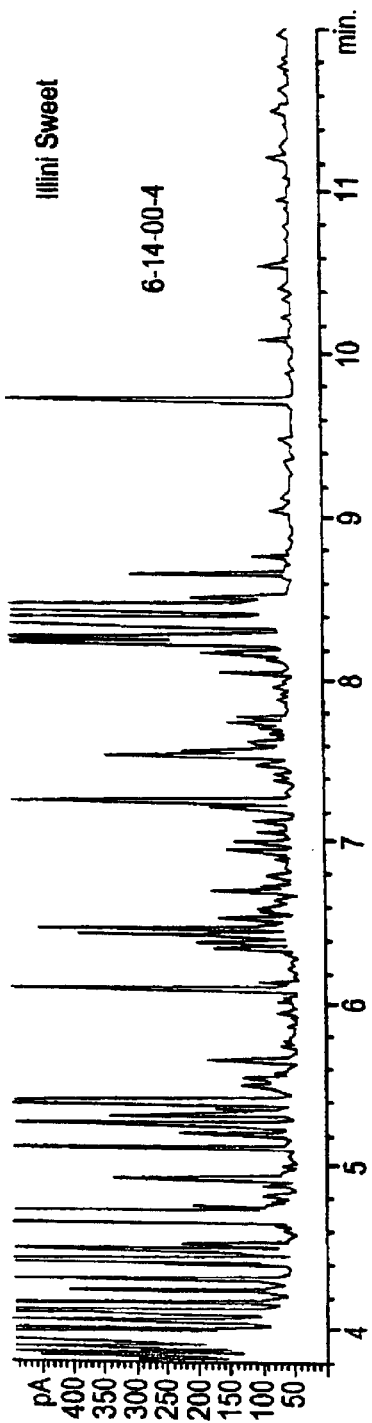
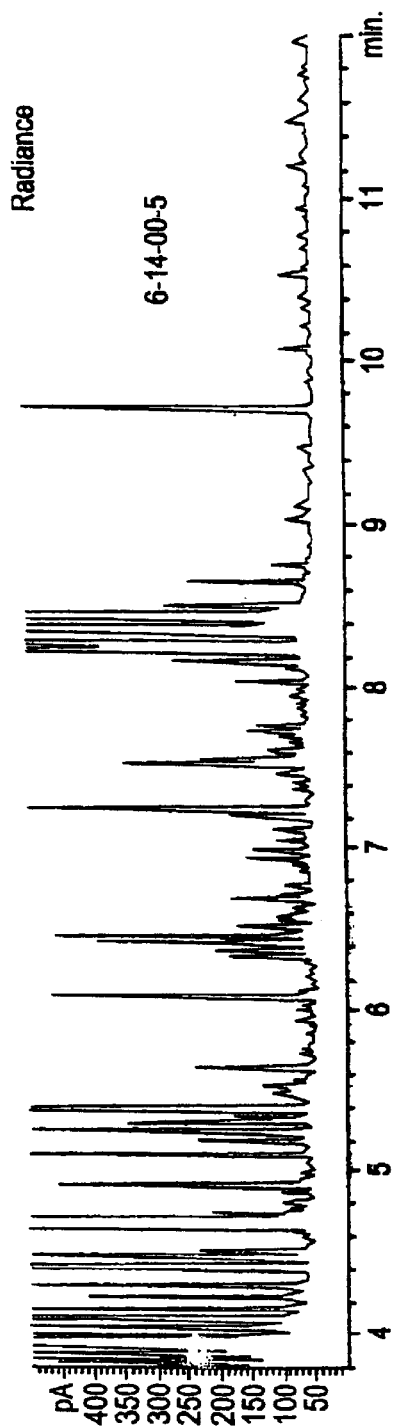

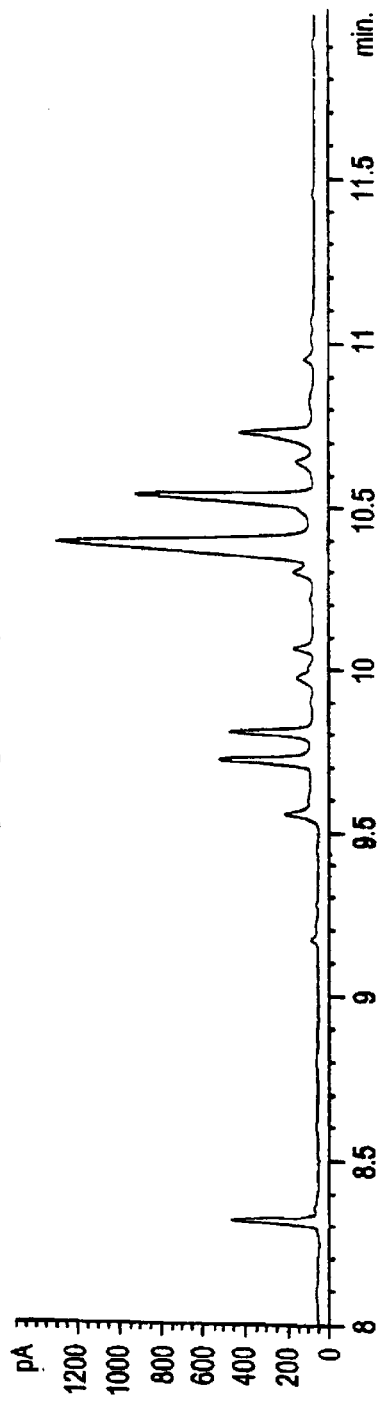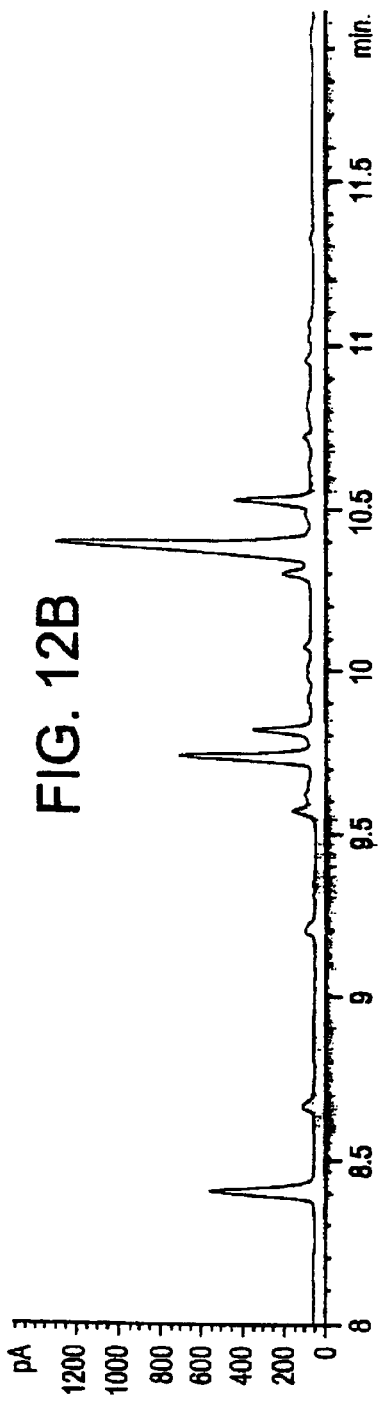
FIG. 12A
FIG. 12B

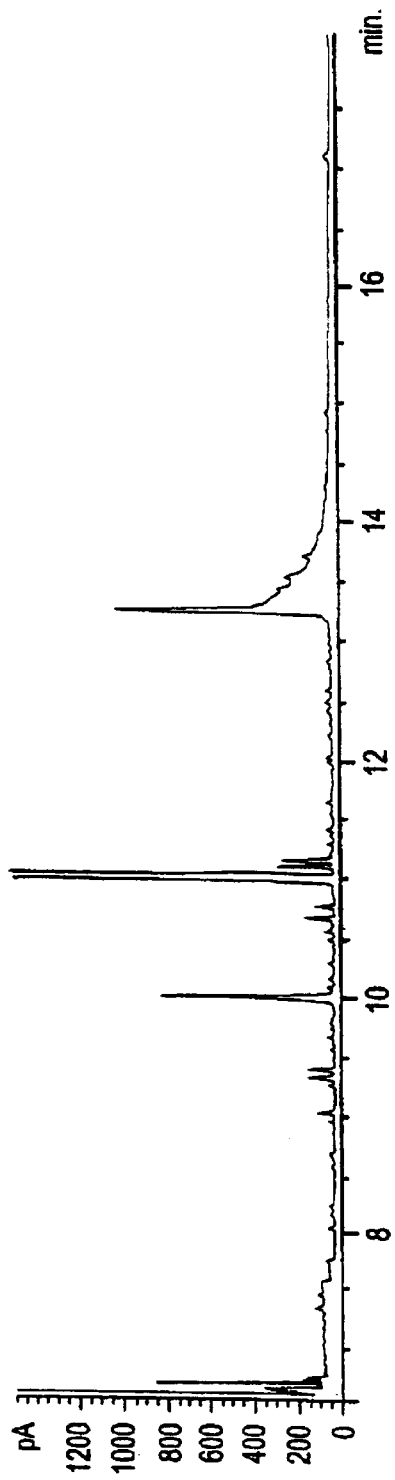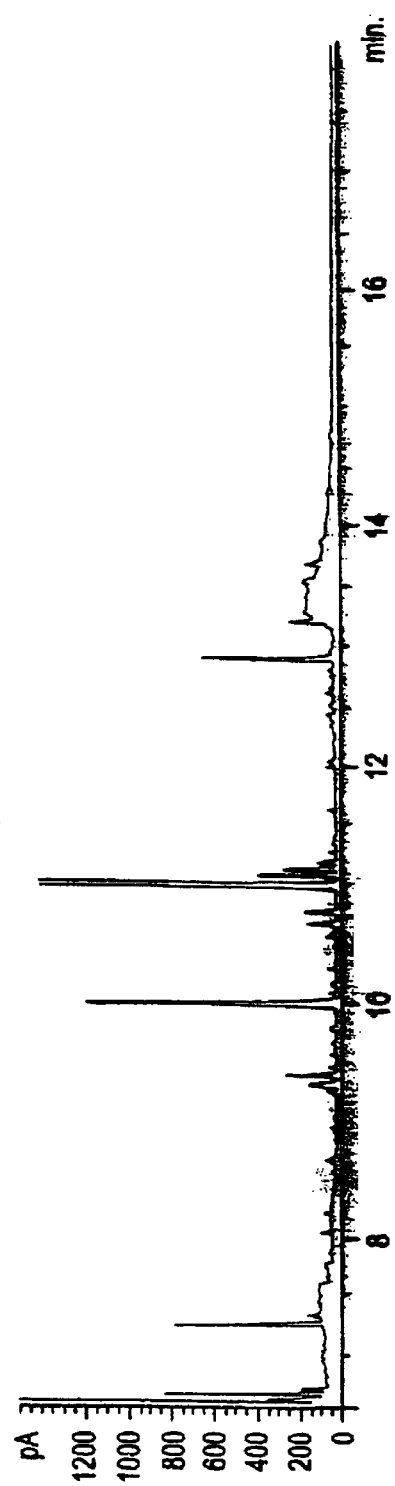

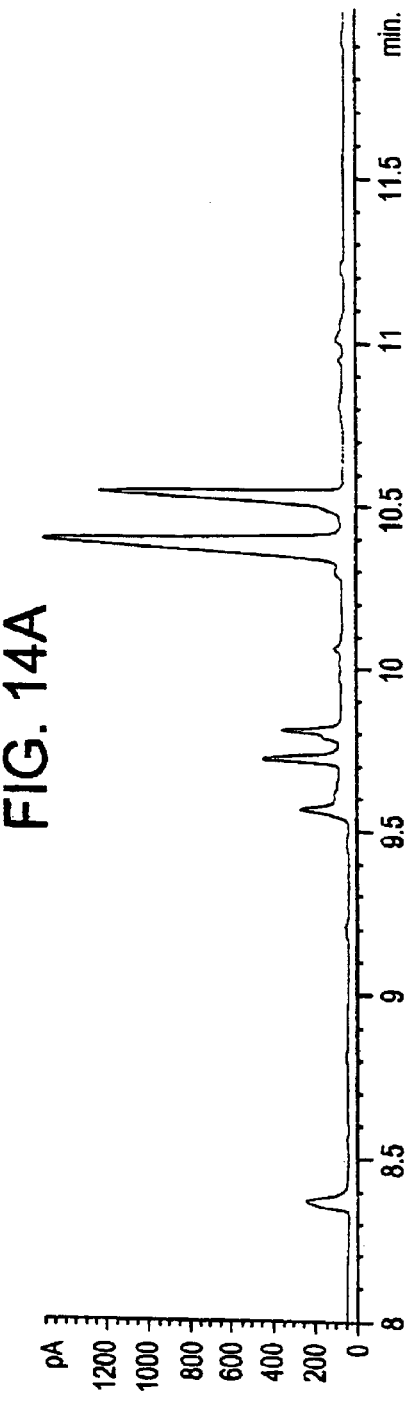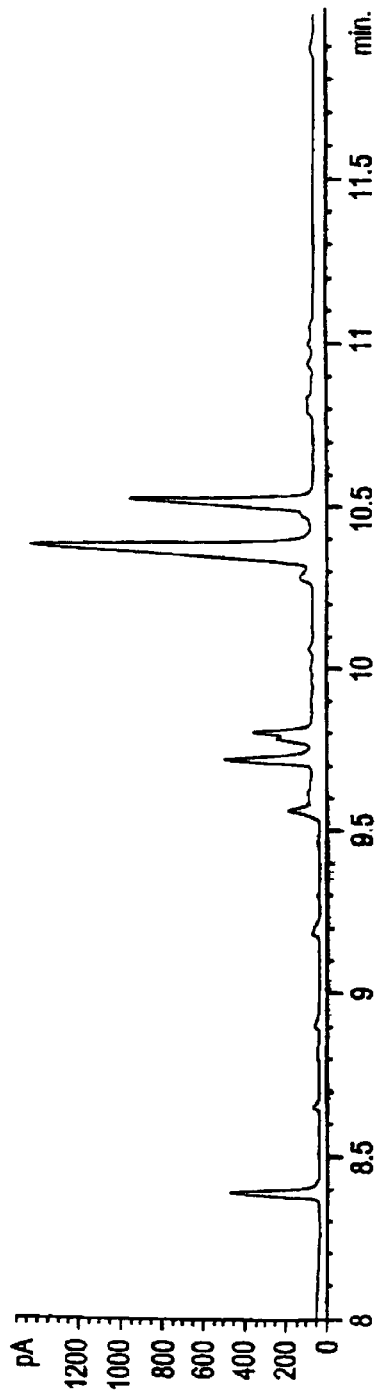

METHOD FOR CHEMICAL ANALYSIS OF BIOLOGICAL MATERIAL

CROSS-REFERENCE TO RELATED APPLICATION

The Instant Application is a Continuation-in-Part of U.S. Provisional Patent Application S/No. 60/143,533 filed Jul. 13, 1999.

BACKGROUND OF THE INVENTION

The instant invention is in the field of methods for chemical analysis of biological material and more specifically the instant invention is in the field of methods for determining chemically related differences between subject biological material and control biological material by way of separation techniques such as chromatography.

It is common practice to extract various chemical compounds from biological materials (such as leaves and/or stems and/or seeds from a plant) by contacting the biological material with a fluid extractant such as hexane or water. The extract may then be chromatographed, for example, by gas chromatography or liquid chromatography, to produce a chromatogram. The chromatogram indicates the separation and detection of the extracted chemical compounds.

Existing chemical analysis methods for analyzing subject biological material often are directed towards the determination of specific target chemical compound(s). For example, a plant gene may be modified so that the seeds of the plant yield an elevated level of a specific amino acid such as lysine. In this case the chemical analysis method used would target lysine.

However, when an organism is, for example, genetically modified without knowing what changes may result in the chemistry of the organism, then a chemical analysis method is needed which is capable of determining a broad range of chemical compounds. This kind of genetic modification is used, e.g., to determine the activity encoded by a new gene such as may be obtained by techniques well known in the molecular biology art such as gene discovery, gene recombination, gene mutagenesis, and stochastic gene synthesis (i.e. gene formation by random linkage of, e.g., nucleotides, trinucleotides, or secondary-structure-encoding oligonucleotides).

For example, in regard to gene discovery, about 46% of naturally occurring genes sequenced to date by The Institute for Genomic Research TIGR, Rockville, Md.) are of unknown function—being totally new to biology—and about 50% of these are thought to be of broad biological Importance as they have been found conserved among diverse species (according to J. Craig Venter, TIGR Chairman, "Decoding the Human Genome," a public lecture given May 24, 1999 in Midland, Mich.). Defining the nature of such genes, as they function in vivo, would require an efficient method for identifying the in vivo effects—and thus the, e.g., regulatory, biocatalytic, or transductional activities—of the expression products of such genes. Such a method would need to be capable of quickly comparing the concentrations of multiple metabolite species present in cells or organisms modified to contain such genes against the concentrations of multiple metabolite species present in unmodified cells or organisms.

It would be an advance in the art of chemical analysis if a method were developed for determining chemically related differences between subject biological material and control biological material, which method would be capable of determining a broad range of chemical compounds and which method preferably would be capable of rapid and automated use.

SUMMARY OF THE INVENTION

The instant invention provides a method for determining chemically related differences between subject biological material and control biological material which method is capable of determining a broad range of chemical compounds and capable of rapid, automated use. More specifically, the instant invention is a chemical analysis method for determining chemically related differences between subject biological material and control biological material, which method comprises at least the following six steps. The first stop is to contact the subject biological material with a fluid extractant to produce an original fluid extract of the subject biological material. The second step is to contact the control biological material with the fluid extractant to produce an original fluid extract of the control biological material. The third step is to chromatograph the fluid extract of the subject biological material, to produce a chromatogram of the fluid extract of the subject biological material. The fourth step is to chromatograph the fluid extract of the control biological material to produce a chromatogram of the fluid extract of the control biological material. The fifth step is to determine the differences between the chromatograms of the third and fourth steps to identify at least one outlier peak. The sixth step is to determine the chemical identity of the outlier peak, for example, using gas chromatography/mass spectroscopy antis of the outlier peak.

BRIEF DESCRIPTION OF THE DRAWINGS

FIGS. 1A–1E show various steps for the chromatographic analysis of a subject biological material.

FIGS. 2A–2E show various steps for the chromatographic analysis of a control biological material.

FIG. 3 is a flow diagram illustrating a preferred embodiment of the chromatographic method of the present invention.

FIG. 4 is a flow diagram illustrating a preferred embodiment of the chromatographic method of the present invention.

FIG. 5 is a flow diagram illustrating a preferred embodiment of the chromatographic method of the present invention.

FIGS. 6A–6B show representative Fraction 1 chromatograms obtained for subject and control Burley tobacco, and FIGS. 6C–6D show a comparison with a GC-MS chromatogram of squalene demonstrating the squalene concentration in Fraction 1 of subject Burley tobacco.

FIGS. 8A–8E show representative Fraction 1 chromatograms obtained for various corn samples.

FIGS. 9A–9E show representative Fraction 2 chromatograms obtained for various corn samples.

FIGS. 10A–19E show representative Fraction 3 chromatograms obtained for various corn samples.

FIG. 12A shows a chromatogram of fatty acid methyl esters from a Fraction 2 extract from *Candida tropicalis* with glucose feed, and FIG. 12B shows a chromatogram of fatty acid methyl esters from a Fraction 2 extract from *Candida tropicalis* with dodecane feed.

FIG. 13A shows a chromatogram of a Fraction 1 extract from *Yarrowia lipolytica* with glucose feed, and FIG. 13B shows a chromatogram of a Fraction 1 extract from *Yarrowia lipolytica* with dodecane feed.

FIG. 14A shows a chromatogram of fatty acid methyl esters from a Fraction 2 extract from *Yarrowia lipolytica* with glucose feed, and FIG. 14B shows a chromatogram of fatty acid methyl esters from a Fraction 2 extract from *Yarrowia lipolytica* with dodecane feed.

DETAILED DESCRIPTION OF THE INVENTION

Figure 7A:
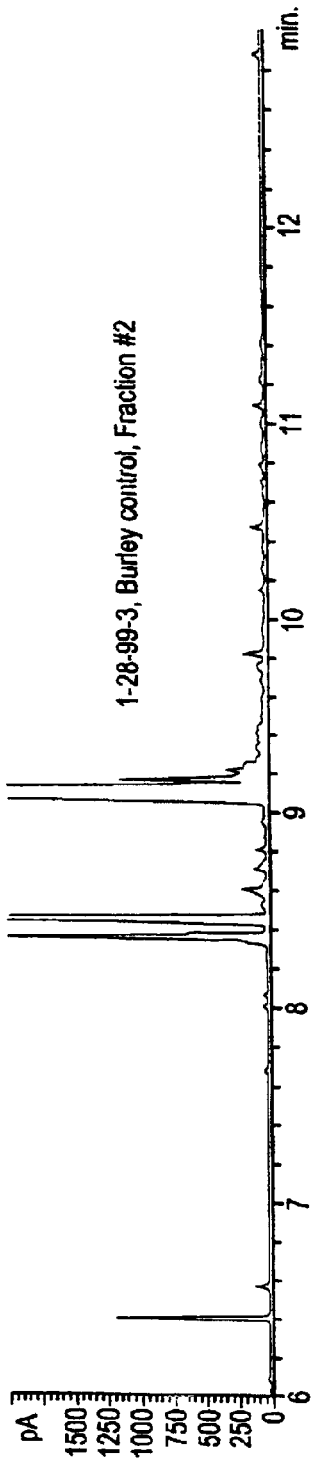
FIGS. 7A–7B show representative Fraction 2 chromatograms and FIGS. 7C–7D show representative Fraction 3 chromatograms obtained for subject and control Burley tobacco.
Figure 7B:
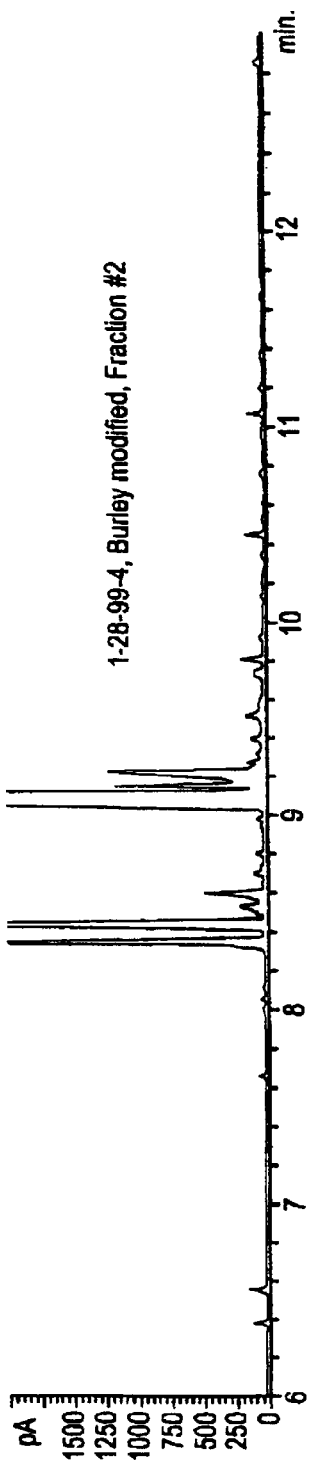
Figure 7C:
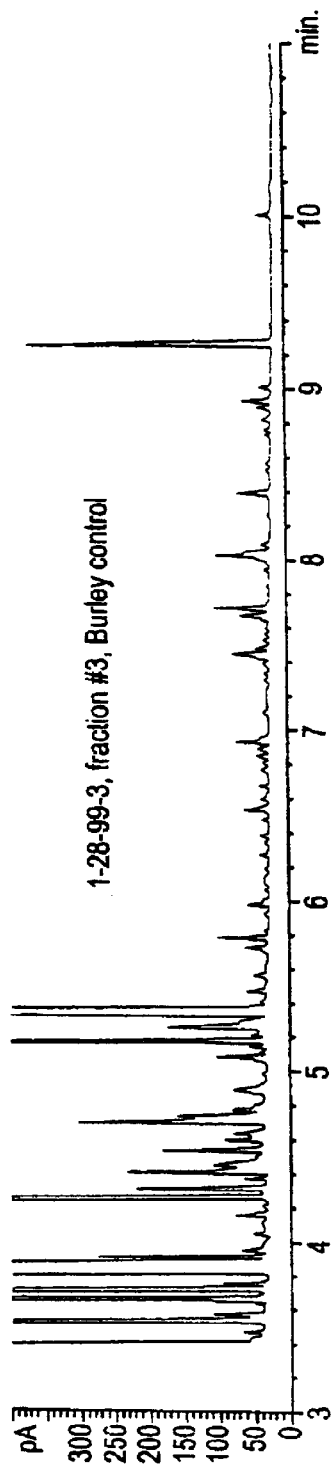
Figure 7D:
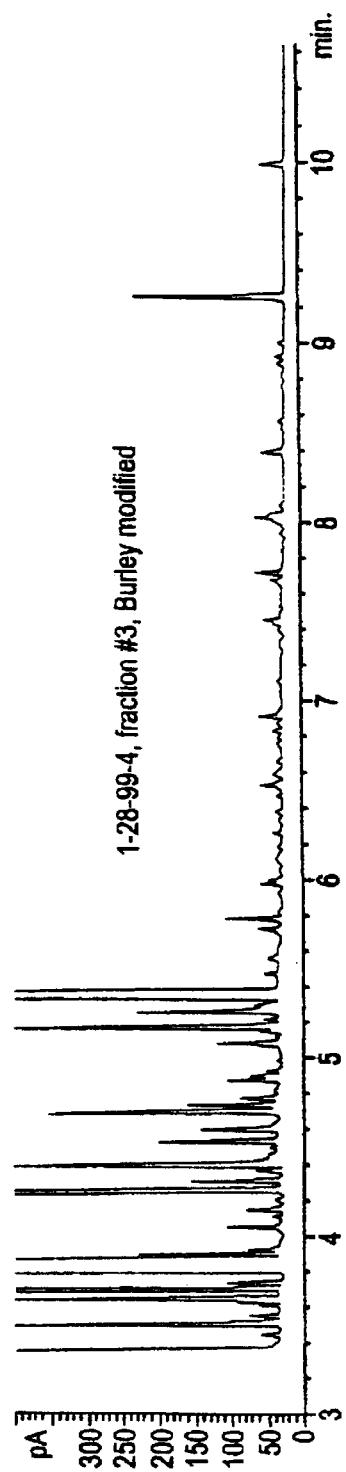
Figure 8A:
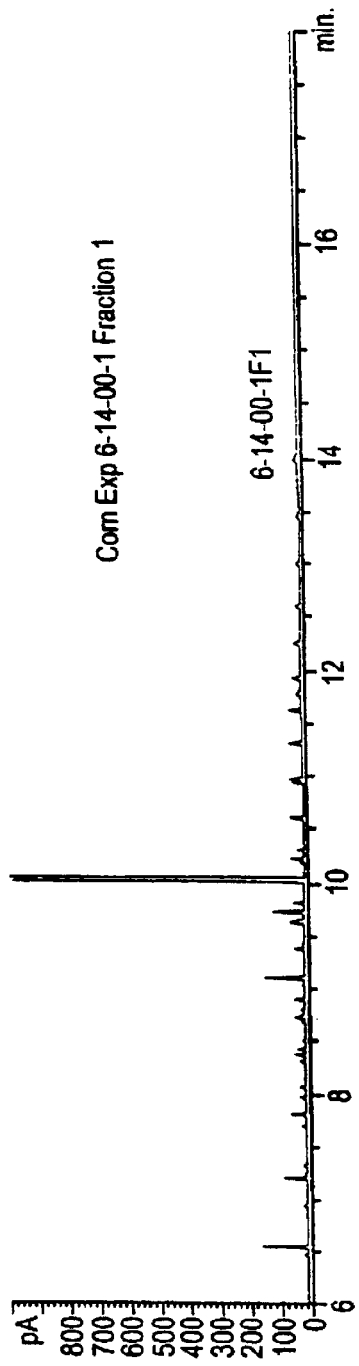
Figure 8B:
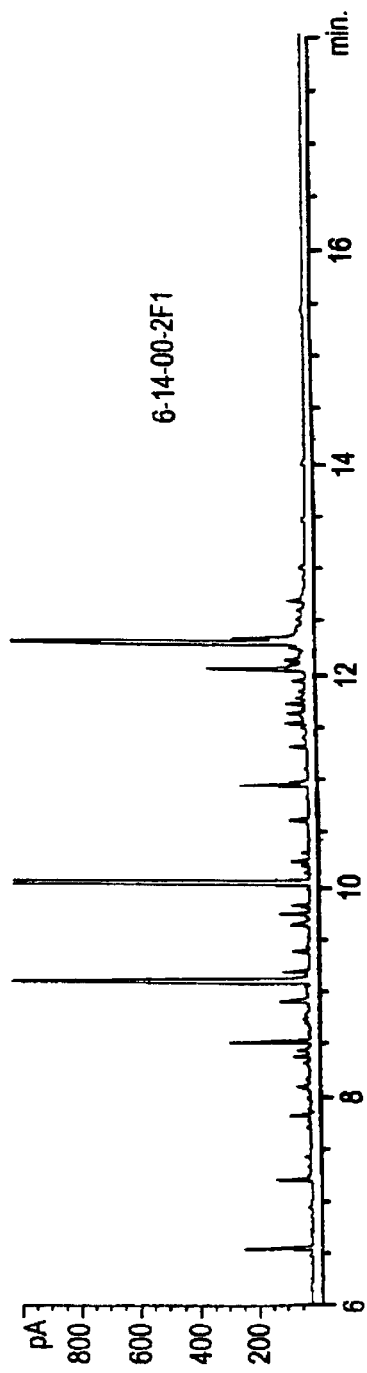
Figure 8C:
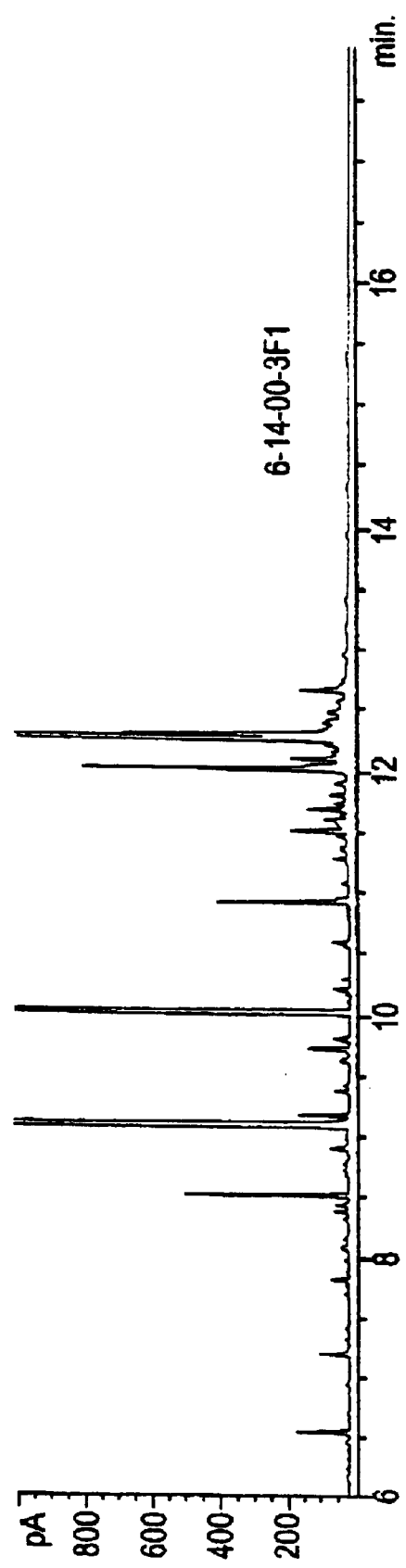
Figure 9A:
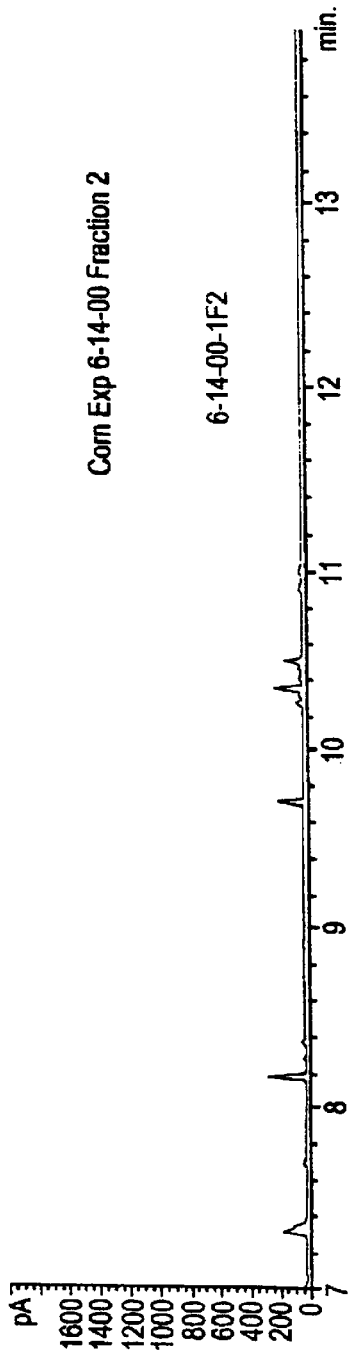
Figure 9B:
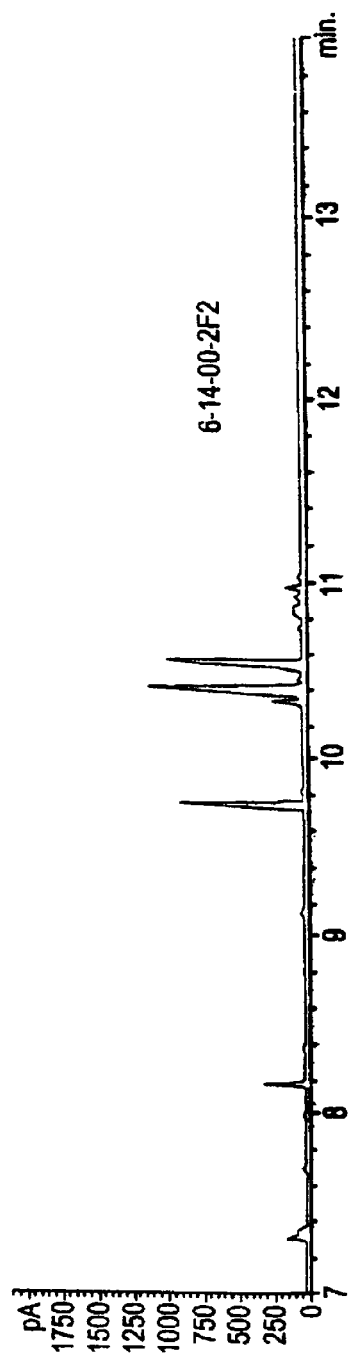
Figure 9D:
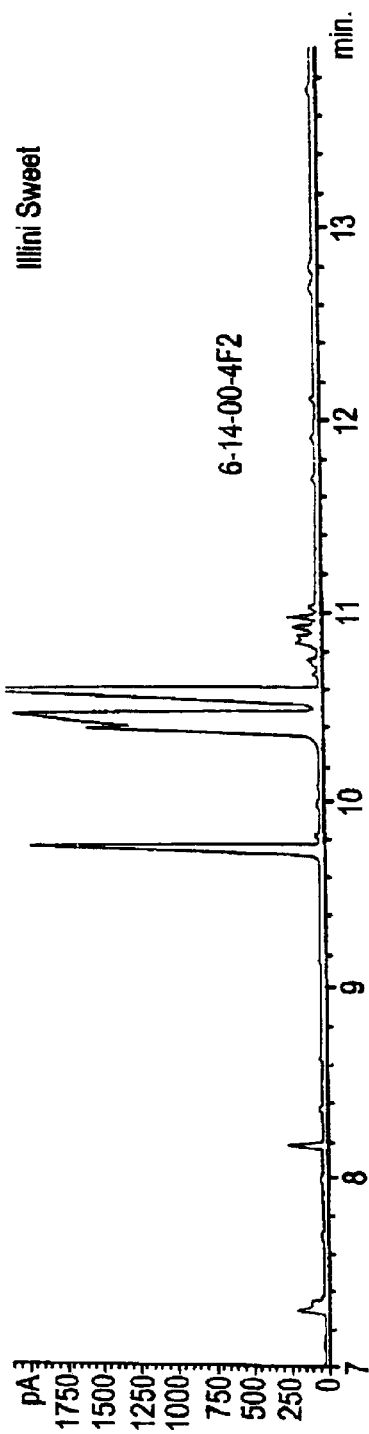
Figure 9E:
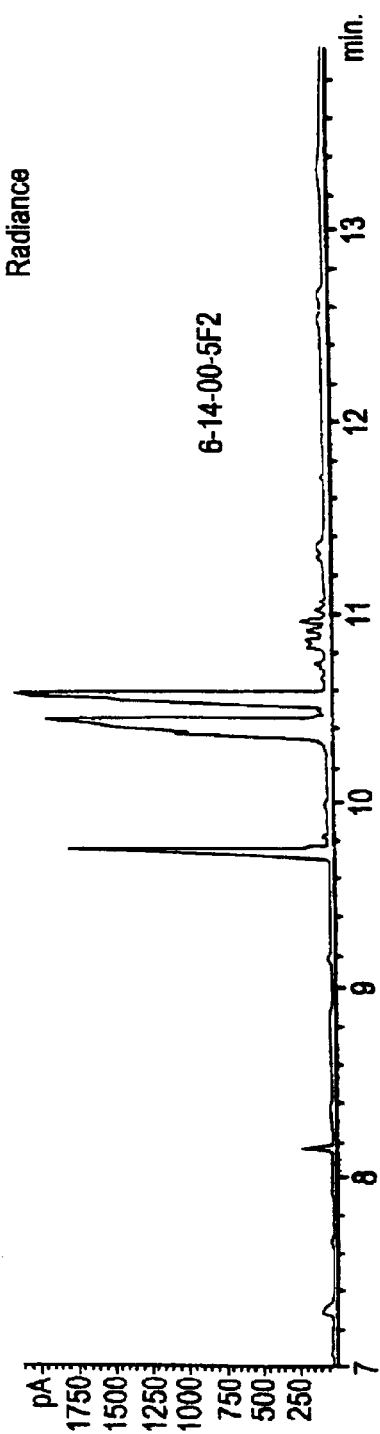
Figure 10A:
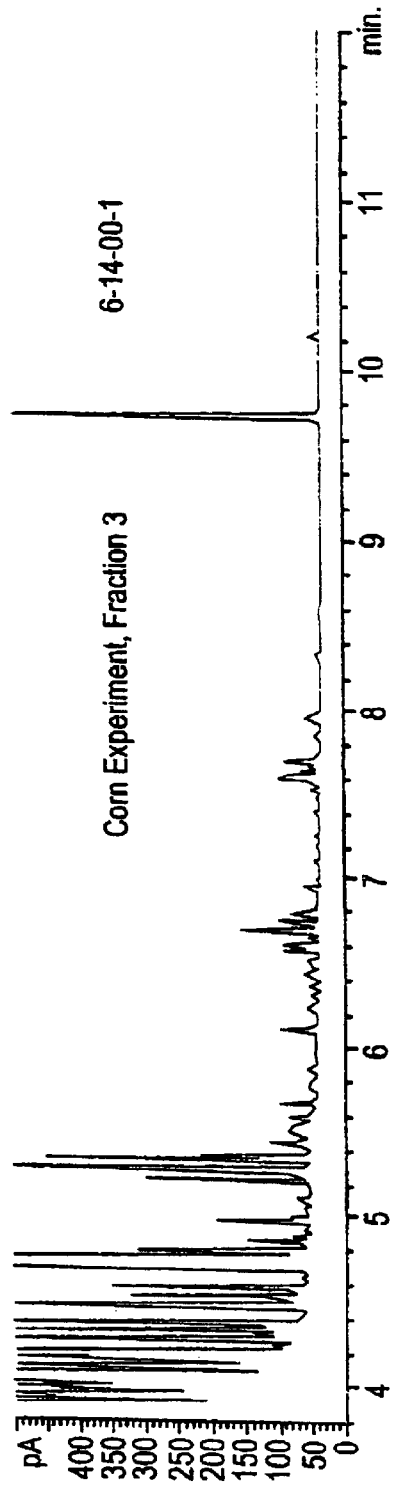
Figure 10B:
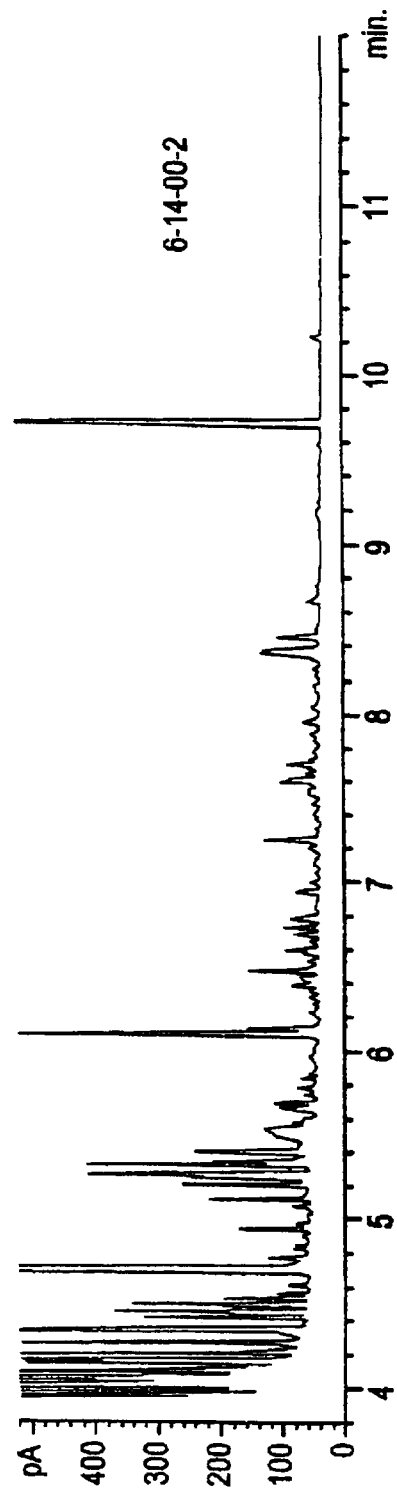
Figure 10C:
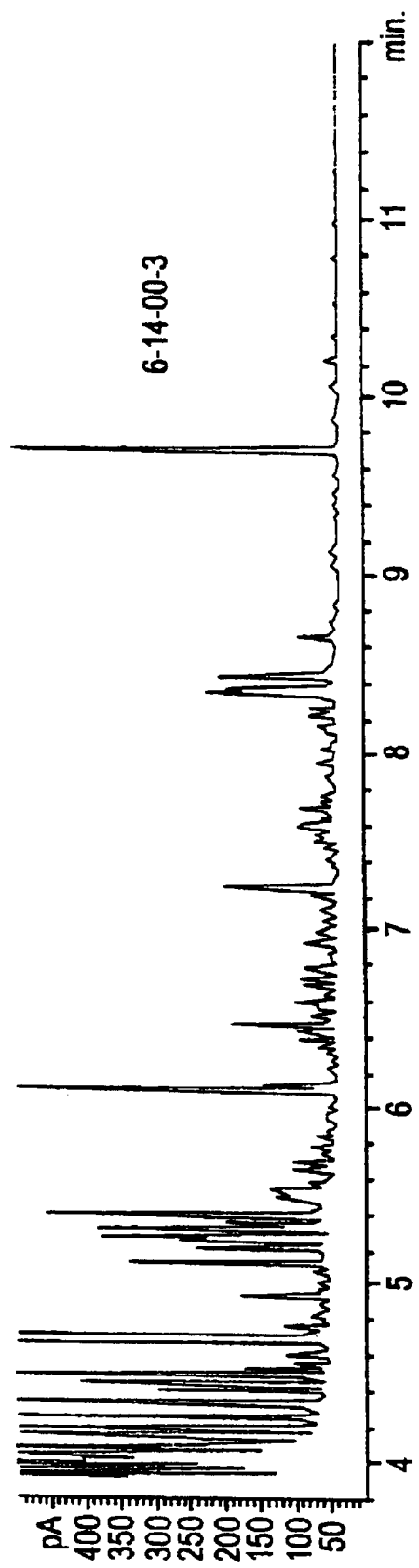

Various terms as used herein are defined as follows.

Biological Material

The term "biological material" means: a portion or portions of one or more cells, organs, or organisms; a whole cell, organelle, organ, or organism; or a group of cells, organelles, organs, or organisms. For example, if the organism(s) supplying the biological material is a garden variety carrot, a single leaf of one carrot plant could be used, or one or more whole carrot plant(s) could be used, or partial or whole taproots from a number of different individuals could be used, or mitochondria extracted from the crown of one carrot plant could be used.

The organism from which the biological material is obtained may be any naturally-occurring or artificially manipulated organism (however propagated or grown). Such an organism may be selected from among the eukaryotes and prokaryotes. Exemplary eukaryotes include, e.g.: fungi (including, e.g., yeasts), vascular and non-vascular plants, animals, and protists (including, e.g., algae, protozoans, zooplankton, phytoplanklon, mildews, single-called animals, amitochondrial eukaryotes). Exemplary prokaryotes include, e.g.: eubacteria (including, e.g., heterotrophic bacteria; cyanobacteria, prochlorophytes, and other photosynthetic bacteria; mycoplasms) end archaeabacteria (including, e.g., halophiles, thermophiles, and methanogens).

Where the organism supplying the biological material is a unicellular or simple multicellular organism, typically a group of whole organisms will be used; however, well-known biochemical techniques (for example, cellular disruption followed by density gradient centrifugation) can be used to extract from any uni- or multi-cellular organism(s) a group of organelles or other cellular parts for use as the biological material, groups of the same structures or groups of a variety of structures. For example, various membrane-bound structures such as nuclei, mitochondria, inclusion bodies, vacuoles, vesicles such as lysosomes and peroxisomes, and/or plastids such as chloroplasts and chromoplasts, may be obtained in such a manner.

The terms "control biological material" and "subject biological material" both refer to biological material taken from (cultivated/domesticated or uncultivated/non-domesticated wild-type or genetically modified) individual (s) of any taxonomic category or categories, i.e. kingdom, phylum, subphylum, class, subclass, order, suborder, family, subfamily, genus, subgenus, species, subspecies, variety, breed, or strain.

The "control" and "subject" biological material may be, and typically are, taken from individual(s) of the same taxonomic category, preferably from the same species, subspecies, variety, breed, or strain. However, when comparison between different types of organisms is desired, the "control" and "subject" biological material may be taken from individual(s) of different taxonomic categories.

The "control" and "subject" biological materials differ from each other in at least one way. This difference may be that the "control" and "subject" biological materials were obtained from individual(s) of different taxonomic categories. Alternatively, or additionally, they may be different parts of the same organ(s), they may be different organelles or different groups of organelles, different cells or different groups of cells, different organs or different groups of organs, or different whole organisms or different groups of whole organisms. The difference may be that the organisms providing the biological materials are identical, but for, e.g., their growth stages.

Preferably, the cell(s)s, organelle(s), organ(s), or organism(s) providing the "control" and "subject" biological material are or are from individual(s) of the same species, subspecies, variety, breed, or strain, and preferably the "control" and "subject" individual(s), organ(s), or organelle (s) differ in their treatment, more preferably they differ only in their treatment. Types of such "treatment" include, but are not limited to, one or more of the following:

A. Culture mode, e.g.: aqua-cultured, soil cultured, broth fermented, agar-cultured.

B. Growing conditions, e.g.: degree of or change in temperature; amount or kind or delivery mode of or change in watering/hydration, lighting/darkness/sleep, diet/salinity/ nutrients, or atmospheric gases; time between fertilization or germination and harvest; aggressive or minimal soil cultivation/husbandry/grooming; environment/growth medium/soil composition or type; altitude; population density; ecological neighbors; exposure to insects, microbes, virus/phage, or disease(s).

C. Adaptation to growing conditions, e.g.: greenhouse-adapted, field-adapted, barn-adapted, photosynthesizing, carbon-source-dependent; cultivated/domesticated; uncultivated/non-domesticated.

D. Propagation mode, e.g.: sexual propagation by human-assisted or human-unassisted fertilization, seed germination, or spore germination: asexual propagation such as grafting, cloning, tissue culturing, cell fusion.

E. Application of chemicals/biochemicals/ pharmaceuticals; e.g.: inoculants, vaccines, antibiotics, growth hormones, growth promoters, herbicides, pesticides, germicides, virucides, oils/waxes, radiolabeled precursors, toxins, waste-products; formulation of substance applied; site (e.g., organ or system), frequency, and mode of application (e.g., ingestion/imbibition/absorption/injection, topical application, transcuticuar/transdermal/transmembranous application, time-released or single or multiple application); time between application and harvest.

F. Degree of tissue differentiation, e.g.: totipotent material versus reversibly differentiated versus permanently differentiated material.

G. Harvest and Post-Harvest factors, e.g.: harvest, isolation, or purification method; post-harvest storage conditions; post-harvest tissue culturing of, e.g., organ(s) or cells; post-harvest tissue culture conditions; post-harvest preservation method, e.g., chemical treatment, cooking, smoking, drying, freezing, flash-freezing, freeze-drying, irradiating; amount of time spent in the post-harvest stored/preserved/cultured state before analysilis.

H. Genetic modification, e.g.: hybridization; nucleic acid transfer by cell-to-cell conjugation; inter-taxonomic-category cell fusion; genetic mutation and/or recombination by application of mutagenizing and/or recombination agents, and/or by use of mutation-fostering and/or recombination-fostering conditions, e.g., permanent or transient mismatch-repair system inactivation; insertion/transfection/infection of naked, or vector-, virus-, or bacteriophage-containing, or other-carrier-associated nucteic acid(s) into cell(s), organelle(s), organ(s), or organism(s). Such vectors include, e.g., plasmids, cosmids, phagemids (phage containing a plasmid replicon), phasmids (phage-plasmid hybrids), phosmids (phage-cosmid hybrids), and artficial chromosomes; "other carriers" include, e.g., histone-like particles, and gene gun pellets.

I. Other factors, e.g.: length of and/or course of any treatment(s); timing of tratment(s), e.g., pre-fertilization, pre-germination, pre-maturation, pre-harvest, or post-harvest timing.

Preferably, the "subject" biological material differs from the "control" biological material only in that the former is taken from individual(s) which have been treated in order to attempt to alter the chemistry thereof, while the latter is taken from an individual(s) having not received such treatment. However, in an alternative embodiment, two or more "subject" biological materials, each of which is taken from a different individual(s) having received a different treatment, may be analyzed and compared to one another, in which case, any on of these may be arbitrarily assigned as a "control" biological material.

Preferably, the treatment given the individual(s) providing the "subject" biological material (and preferably withheld from the "control" biological material) comprises genetic modification. Genetic modification may comprise the use of, e.g., hybridization or cross-breeding, mutagenesis (e.g., chemical-induced or radiation-induced mutation), site-directed mutation, DNA repair system inhibition or deficiency, homologous recombination, site-directed recombination, and/or other techniques known in the art as effective for modifying the genes within a cell, organelle, organ, or organism. More preferably, such genetic modification comprises insertion or transfection or infection of nucleic acid(s) into the cell(s), organelle(s), organ(s), or organism(s) which are or which will provide the "subject" biological material. Examples of such nucleic acids include, but are not limited to: naked nucleic acids, vectors (e.g.: plasmids, transposes; hybrid vectors such as plasposons, cosmids, phagemids, phasmids, phosmids, fosmids; artficial chromosomes such as YACs, PACs, BACs, MACs; bacteria such as Agrobacterium tumefaciens, A. rhizogenes), virus, phage, and carriers containing or coated with nucleic acids (e.g., liposomes, cationic lipids, cationic polymers).

In one embodiment, the biological materials are obtained from a prokaryote or prokaryotes (including archaeabacteria, cyanobacteria, and heterotrophic bacteria). In another embodiment, the biological materials are obtained from a eukaryote or eukaryotes, preferably plants or fungi, more preferably plants. In this embodiment, any plants may provide the biological material, including single-celled plants, non-vascular plants, non-Flowering vascular plants (whether spore plants or seed plants), and flowering plants; examples of such plants include: mosses, club moss, ferns, horsetails, liverworts, gymnosperms, monocots, dicots, and other plants (algae, which are classified as protists, may also be considered as plants in this regard).

Chemically-Related Difference

The term "chemically related difference" means a difference between "subject" and "control" biological material which can be detected by comparison of a chromatogram of metabolites (or derivatives of metabolites) extracted from the "subject biological material" with a "control chromatogram" of metabolites (or derivatives of metabolites) extracted from the "control" biological material. Such a difference could be, e.g., the presence or absence of a metabolite, or the significant increase or decrease in quantity of a metabolite.

Chromatogram

The term "chromatogram" as used herein means an electronic and/or graphic record of data representing the absolutely or relatively quantitative detection of a plurality of separated chemical species obtained or derived from a group of metabolites, whether or not such separation has been performed by chromatography or some other method (e.g., to electrophoresis).

The term "control chromatogram" as used herein means an individual chromatogram, or an average or model chromatogram based on multiple individual chromatograms, of chemical species obtained from a group of metabolites extracted from "control" biological material. The term "subject chromatogram" as used herein means an individual chromatogram, or an average or model chromatogram based on multiple individual chromatograms, at chemical species obtained from a group of metabolites extracted from a "subject" biological material. In either case, a model chromatogram may contain data including, e.g.: peak migration distance (or elation time) ranges and averages; peak height and peak area ranges and averages; and other parameters.

Genetically modified

The terms "genetically modified" and "genetically unmodified" when used in relation to subject biological material and control biological material, respectively, refer to the fact that the subject biological material has been treated to produce a genetic modification thereof, whereas the control biological material has not received that particular genetic modification. In this context, the term "genetically unmodified" does not Imply that the "control" biological material must be, e.g., a naturally-occurring, wild-type plant; rather, both the control and subject biological materials may be (but need not be) the result of, e.g., hybridization, selection, or genetic engineering.

Metabolome

As used herein, the term "metabolome" indicates the complement of relatively low molecular weight molecules that is present in a plant, plant part, or plant sample, or in a suspension or extract thereof. Examples of such molecules include, but are not limited to: acids and related compounds; mono-, di-, and tri-carboxylic acids (saturated, unsaturated aliphatic and cyclic, aryl, alkaryl); aldo-acids, keto-acids; lactone forms; gibbereillins; abscisic acid; alcohols, polyols, derivatives, and related compounds; ethyl alcohol, benzyl alcohol, menthanol; propylene glycol, glycerol, phytol; inositol, furfuryl alcohol, menthol; aldehydes, ketones, quinones, derivatives, and related compounds; acetaldehyde, butyraldehyde, benzaldehyde, acrolein, furfural, glyoxal; acetone, butanone; anthraquinone; carbohydrates; mono-, di-, tri-saccharides; alkaloids, amines, and other bases; pyridines (including nicotinic acid, nicotinamide); pyrimidines (including cytidine, thymine); purines (including guanine, adenine, xanthines/hypoxanthines, kinetin); pyrroles; quinolines (including isoquinolines); morphinans, tropanes, cinchonans; nucieotides, oligonucleotides, derivatives, and related compounds; guanosine, cytosine, adenosine, thymidine, inosine; amino acids, oligopepides, derivatives, and related compounds; esters; phenols and related compounds; heterocyclic compounds and derivatives; pyrroles, tetrapyrroles (corrinoids and porphines/porphyrins, w/w/o metal-ion); flavonoids; indoles; lipids (including fatty acids and triglycerides), derivatives, and related compounds; carotenoids, phytoene; and sterols, isoprenoids including terpenes.

Outlier Peak

The term "outlier peak" as used herein indicates: a peak in a subject chromatogram that has a significantly different peak height or area than the corresponding peak in a control chromatogram; or a peak in a subject chromatogram that is not present in a control chromatogram; or a peak that is missing from a subject chromatogram although present in a control chromatogram.

Referring now to FIGS. 1A–1E, therein is shown various steps for the chromatographic analysis of a subject biological material 10. As shown in FIG. 1A, the subject biological material 10 is contacted with a fluid extractant 11 contained for example, in container 12 to produce a fluid extract 13 of the subject biological material. The extract 13 is then chromatographed, for example by using syringe 14 to inject a portion of extract 13 into the chromatograph 15 as shown in FIG. 1C, to produce a chromatogram, for example, the chromatogram shown in FIG. 1D. Preferably, this procedure is repeated to increase the statistical reliability of the results.

The specific fluid extractant used in the instant invention comprises a C3 alcohol, preferably isopropanol. Preferably, the extractant also comprises water, i.e. comprises an aqueous C3 alcohol, more preferably aqueous isopropanol. Preferably the aqueous isopropanol used in the extractant is from about 10% to about 90% by volume isopropanol.

In a preferred embodiment, the fluid extractant is a mixture of water and isopropanol. In this embodiment, the aqueous isopropanol is preferably about 25% to about 75% by volume isopropanol, more preferably about 70% isopropanol.

In an alterative preferred embodiment, the fluid extractant is a mixture of water, isopropanol, and potassium hydroxide. In this embodiment the aqueous isopropanol is preferably about 25% to about 75% by volume isopropanol, more preferably about 50% isopropanol; and the KOH is present in the extractant is an amount sufficient to result in a final concentration of about 0.01–0.5N KOH, more preferably about 0.05–0.2N KOH, and still more preferably about 0.1N KOH.

Other solvent or solution components may also be present in the extractant, and where used, are preferably selected so as to be misable with all other solvents or solutions in the extractant. For example, surfactants may be added to the extractant.

Prior to extraction, the subject and control biological material(s) may be prepared. Such preparation may include, e.g., freezing, drying, lyophilizing, cutting, chopping, shredding, crushing, grinding, blending, homogenizing, sonicating, and other techniques known in the art that may be used to convert the form of the biological material to that desired for use in extraction. Alternatively, the biological material(s) may be pre-treated before extraction by removing a portion or portions therefrom and reserving the portion(s) for the purpose of, e.g., future repeat tests or alternative testing. For example, where the biological material is a macroscopic tissue, such as a plant leaf, the tissue may be pre-treated to reserve surface metabolites (such as, e.g., epidermal or cuticular oils and waxes), in order to assay these by an alternative test: the tissue may be transitorily dipped into an organic solvent such as hexane to remove these surface metabolites. Likewise, a portion of the biological material, e.g., a cut-out portion of leaf tissue, may be reserved from the remainder to be extracted.

In the process of extracting the subject and control biological material(s), the contacting of the biological material(s) with the extractant may be carried out in one or more of various ways. Soaking of the biological material in the extractant to produce, e.g., a leachate may also be used. Supercritical fluid extraction may be used. Other techniques that may be used in the process of contacting include, e.g., cutting, chopping, shredding, crushing, grinding, blending, homogenizing, and sonicating. In any embodiment, the extraction will result in production of original fluid extracts of the control and subject biological materal(s).

These original extracts may be chromatographed as is, or further derivatized or fractionated prior to chromatographing the derivatives or fractions of the original extract. In a preferred embodiment, the original fluid extracts of the control and subject biological material(s) are first fractionated prior to chromatography, and the fractions are then chromatographed. Fractions so obtained may also be further treated, e.g., to derivative chemical species present therein, prior to chromatography, so that it is the derivatized fractions that are chromatographed. Referring now to FIG. 1E, the extract 13 is contacted with a liquid solvent, for example in container 16, to produce a liquid fraction 17 of the subject biological material.

Referring now to FIGS. 2A–2E, therein are shown various steps for the chromatographic analysis of a control biological material 20. As shown in FIG. 2A, the control biological material 20 is contacted with the fluid extractant 11 contained, for example, in container 22 to produce a fluid extract 23 of the control biological material. The extract 23 is then chromatographed, for example, by using syringe 24 to inject a portion of extract 23 into the chromatograph 15 shown in FIG. 2C, to produce a chromatogram, for example, the chromatogram shown in FIG. 2D. Preferably, this procedure is repeated to increase the statistical reliability of the results. Referring now to FIG. 2E, the extract 23 is contacted with the liquid solvent, for example in container 26, to produce a liquid fraction 27 of the control biological material.

The chromatogram shown in FIG. 2D, contains peaks 30, 31, 32, 33 and 34 corresponding ideally to separated individual chemical compounds from the extract of the control biological material. The chromatogram shown in FIG. 1D, contains the same peaks 30, 31, 32, 33 and 34. However, the chromatogram shown in FIG. 1D also shows peak 35 which peak does not appear in the chromatogram shown in FIG. 2D. Peak 35 is an outlier peak.

Outlier peaks can be identified by visual comparison of the chromatograms, whether represented graphically, numerically, or otherwise. However, preferably, outlier peaks are identified by a computer programmed to determine differences between a subject chromatogram and a control chromatogram, e.g., a computer operating a data processing software program. More preferably, the data processing technique used to identify outlier peaks is the data processing technique disclosed in U.S. Pat. No. 5,592,402 herein fully incorporated by reference.

Still more preferably, the data processing technique disclosed in the '402 patent is modified in three ways. First, by dividing the chromatograms into a plurality of elution time regions, e.g., eight to twenty regions, to increase the sensitivity of detection. Second, by augmenting the t-distance calculation with the "Mahalanobis distance" technique (described, for example, by Shah and Gemperline in *Analytical Chemistry*, 62 (1990) pages 465–470, herein fully incorporated by reference) to better identify outlier peaks resulting from the disappearance of a peak(s) in the chromatogram of the extract of the subject biological material relative to the chromatogram of the extract of the control biological material. Third, by incorporating the "correlation optimized warping" technique (described by Nielsen et al. in *Journal of Chromatography*, 805 (1998) pages 17–35, herein fully incorporated by reference) to correct for elution time variations ("drift") of the peaks of the chromatograms.

The order of the contacting steps and the order of the chromatographing steps above are not critical in the instant invention. The first and second steps (contacting) may be done concurrently or the second may be done before the first. Likewise, the third and fourth steps (chromatographing) may be done concurrently or the fourth may be done before the third. However, preferably, steps 2 and 4 are performed first and steps 1 and 3 second, i.e. preferably the control biological material is contacted with the extractant and the control extract is chromatographed first before extracting and chromatographing the subject biological material.

Preferably, at least two aliquots of the control extract are separately chromatographed and/or multiple control extracts are made and separately chromatographed, so that multiple chromatograms provide a statistically characterized basis for comparison with the subject chromatogram, i.e. such as an average or model control chromatogram. Preferably, this average or model control chromatogram includes analyte peak migration distance (or elution time) ranges and analyte peak height and/or peak area ranges. This control chromatogram is then used as the basis of comparison with the subject chromatogram produced by chromatography of the extract of the subject biological material.

The specific type of chromatography used in the instant invention is not critical. Useful separation methods employ a fluid moving phase and either a solid or liquid stationary phase. For example, the separation methods useful herein include: gas chromatography (including pyrolysis chromatography, subtraction chromatography, and other gas chromatography methods); liquid chromatography (including normal phase, reverse phase, high pressure, and other liquid chromatography methods); partition chromatography (including liquid partitioning chromatography); ion chromatography and electro-chromatography; countercurrent or hydrodynamic chromatography; thin layer chromatography; supercritical fluid chromatography; exclusion chromatography (including gel permeation chromatography); and capillary electro-chromatography. However, in its full scope, the instant invention includes any separation technique and is not limited to chromatographing the extracts or fractions. Thus, electrophoresis may be used, especially where separation of ionic species is desired. Combinations of various separation techniques may be used; also multi-dimensional separations may be performed. In one embodiment, preferably liquid chromatography is used. In another embodiment, preferably gas chromatography is used because a gas chromatograph may effectively be coupled to a mass spectrometer.

The technique for determining the chemical identity of an outlier peak may be selected from any known in the chemical analysis art. Gas chromatography/mass spectroscopy is a powerful and well developed technique which is preferably used in the instant invention to determine the chemical identity of an outlier peak. However, when it is better to use, e.g., liquid chromatography for such a determination, then the chemical identity of the outlier peak may be determined by a number of techniques such as by UV-Vis spectroscopy, fluid chromatography/mass spectroscopy, and peak trapping followed by various isolation and identification techniques well known in the chemical analysis art. In some cases, the migration distance (or elution time) of an analyte can provide a basis for positive identification of the chemical species thereof.

The method of the instant invention may be partly or entirely automated. For example, one or more of the extraction, separation, outlier peak determination, and outlier peak identification steps may be automated. In some cases, even the step of providing the control and subject biological materials can be automated (e.g., where a robot or other machine selects and/or processes an organism or part thereof, resulting in provision of the biological material). Although the fluid extract of the subject and control material may be directly chromatographed as described above, preferably these extracts are contacted with a liquid solvent or solvents, which liquid solvent(s) is not miscible with the extract to produce one or more liquid fraction. The liquid fraction(s) may then be chromatographed.

It should be understood that the instant invention provides the ability to relate the chemically related differences to genetic modifications. For example, single or multiple metabolites may be Identified and related to predicted or unanticipated gene function, whether resulting from gene expression or gene inactivation. In addition, the appearance of a specific metabolite may be indicative of enzymatic activity without the need for classic, specific enzymatic assays of the biological material. Genomes of plants, microbes, fungi, and various other organisms, display rich secondary metabolism which can be explored using the instant invention.

Examples of metabolites that may be analyzed by the instant invention include, but are not limited to:

Acids and Related Compounds

Mono-, di-,and ti-carboxylic acids (saturated, unsaturated, aliphatic and cyclic, aryl, alkaryl)

Aldo-acids, Keto-acids

Lactone forms

Gibberellins

Abscisic Acid

Alcohols, Polyols, Derivatives, and Related Compounds

Ethyl alcohol, benzyl alcohol, menthanol

Propylene glycol, glycerol, phytol inositol, furfuryl alcohol, menthol

Aldehydes, Ketones, Quinones, Derivatives, and Related Compounds

Acetaldehyde, Butyraldehyde, Benzaldehyde, Acrolein, Furfural, Glyoxal

Acetone, Butanone

Anthraquinone

Mono-, Di-, Tri-, and Oligo-Sacoharides, Derivatives, and Related Compounds

Alkaloids, Amines, and Other Bases

Pyridines (including Nicotinic Acid, Nicotinamide)

Pyrimidines (including Cytidine, Thymine)

Purines (including Guanine, Adenine, Xanthines/Hypoxanthines, Kinetin)

Pyrroles

Quinolines (including isoquinolines)

Morphinans, tropanes, cinchonans

Nucleotides, Oligonucleotides, Derivatives, and Related Compounds

Guanosine, Cytosine, Adenosine, Thymidine, Inosine

Amino Acids, Oligopeptides, Derivatives, and Related Compounds

Esters

Phenols and Related compounds

Heterocyclic Compounds and Derivatives

Pyrroles, Tetrapyrroles (corrinoids and porphines/porphyrins, w/w/o metal-ion)

Flavonoids

Indoles

Lipids, Derivatives, and Related Compounds

Carotenoids, Phytoene

Sterols, Isoprenoids including Terpenes (Degradation products of biopolymer metabolites may also be analyzed)

In a preferred embodiment, the samples of test and control biological material are prepared by freezing and the frozen samples are weighed. The samples are loaded into the extraction cartridges of a Dionex Accelerated Solvent Extraction system model ASE 200 (Dionex Corporation, Sunnyvale, Calif.) which are then filled with a 1:1 water/isopropanol, 0.1N KOH extractant. In an altenative preferred embodiment, a 70% solution of isopropanol is used as the extractant. The samples are automatically extracted at 120 degrees Centigrade and 2,000 pounds per square inch pressure for ten minutes, to produce the original extracts.

Each of the original extracts is contacted with a non-polar organic solvent Preferably, this involves, e.g., mixing, stirring, or shaking. Preferably, the solvent is a C1–C12 organic solvent, examples of which include hexane, octane, methylene chloride, cyclohexane, cyclopentane, hexene, toluene, and benzene. Preferably, the solvent selected will have a boiling point below 120C., more preferably below 11C. More preferably, the solvent is a C5–C8 organic solvent, and still more preferably it is hexane. The solvent may optionally contain a "surrogate" compound which has been added thereto; a preferred surrogate is pentacosane.

Production of Fraction 1

The solvent (e.g., hexane) is then allowed to coalesce into an organic phase, leaving a first aqueous phase. Separation of the organic phase from the aqueous phase results in Fraction 1 (a first organic traction). Fraction 1 is believed to contain, for example, most of the pyridines, indoles, terpenes, phytols, alcohols, and hydrocarbons of the original extract.

Where the fluid extract contains KOH, the aqueous phase is then acidified to a pH below about pH6, more preferably to a pH below pH5, more preferably below pH3. In a preferred embodiment, the aqueous phase is acidified to a pH of about pH1–2, more preferably about pH1. The acidification can be performed using, e.g., a mineral acid (such as HCl, HBr, sulfuric, chlorosulfonic, phosphoric, or nitric) or an organic acid (such as formic, acetic, acetylsulfonic, or benezene sulfonic). Preferably a mineral acid is utilized, more preferably HCl. The resulting acidified aqueous phase is then contacted with a non-polar organic solvent, such as any of those described above in regard to Fraction 1. A preferred solvent is hexane. Preferably, this contacting involves, e.g., mixing, stirring, or shaking. The solvent utilized may optionally contain a "surrogate" compound which has been added thereto; a preferred surrogate is undecanoic acid.

Further Treatment of Fraction 1

Prior to chromatography, Fraction 1 is preferably further treated. Preferably, Fraction 1 is evaporated to dryness, producing a residue. Any evaporative process known effective in the art may be used. In a preferred embodiment, a stream of a gas such as nitrogen or a nobel gas is blown across the surface of the aqueous phase; a preferred gas is nitrogen. More preferably the aqueous phase is brought to an elevated temperature under this stream of gas. In a preferred embodiment, the aqueous phase is brought to about 55 degrees Centigrade, and maintained at that temperature, under a stream of nitrogen gas.

The resulting residue is then reconstituted by addition of a non-polar organic solvent as described above, preferably hexane. This organic solvent may also contain one or more internal standard(s), provided that the internal standards are miscible with the organic solvent. Examples of internal standards include but are not limited to: C10–C36 alkanes; diphenylbenzenes; napthalene, anthracene. Preferably, the internal standard(s) selected are above C14 in size. A preferred internal standard is a diphenylbenzene. A small amount (e.g., 1–2 drops) of dodecane may optionally be, and preferably is, added to the reconstituted Fraction 1 in order to prevent evaporation of volatile components.

Production of Fraction 2

The solvent (e.g., hexane) that had been added to and contacted with the acidified first aqueous phase is allowed to coalesce into an organic phase, leaving a second aqueous phase. Separation of the organic phase from the aqueous phase results in Fraction 2 (a second organic fraction). Fraction 2 is believed to contain, for example, the fatty acids and phenols of the extract. The second aqueous phase is believed to contain, for example, dicarboxylic acids, amino acids, sugars and inorganic compounds.

Further Treatment of Fraction 2

Prior to chromatography, Fraction 2 is preferably further treated. Preferably, Fraction 2 is evaporated to dryness, producing a residue, according to the same evaporation procedures as described for the Further Treatment of Fraction 1. The resulting residue is then reconstituted by addition of a non-polar organic solvent as described above; a preferred solvent is hexane. A small amount (e.g., 1–2 drops) of dodecane may optionally be, and preferably is, added to the reconstituted Fraction 2 in order to prevent evaporation of volatile components.

The reconstituted Fraction 2 is then preferably derivatized by methylation (via transesterification) of, e.g., fatty acid species present therein. Any methylation procedure known effective in the art to methylate fatty acids may be used. In a preferred embodiment an on-column methylation is performed by combining methanol and trimethyl sulfonium hydroxide (TMSOH) with the reconstitute Fraction 2. The presence of these reagents in the reconstituted Fraction 2 will result in methylation of fatty acids when loaded into the heated injector port of a gas chromatograph. In an alternative embodiment, diazomethane is mixed with the reconstituted Fraction 2, to perform an off-column methylation.

Alterative to the Production/Treatment of Fraction 2

In a preferred embodiment, an alternative procedure is used to either substitute for or supplement the above-described procedure for producing and further treating Fraction 2. In this embodiment, a portion of the un-extracted biological material(s) is reserved. This reserved portion is weighed and a C5–C8 alkane is added thereto, preferably heptane. The resulting mixture is then treated to both extract and (trans-)sterify fatty acid species preset therein. The esterification reaction is performed by adding a C1, C2, or C3 alcohol (preferably methanol) and, respectively, a metal C1, C2, or C3 alkoxide (preferably a metal methoxide, more preferably sodium methoxide), and allowing the resulting combination to mix, preferably with stirring or shaking, at room temperature for 30 minutes. Alternatively, the combination may be held at an elevated temperature, at or below boiling, for 30 minutes. At the end of 30 minutes, the reaction is quenched by the addition of water and the alkane phase is allowed to coalesce to form an alkane phase. The alkane phase is the separated off to produce the alternative, treated "Fraction 2." Both the original treated, Fraction 2, and this alternative contain alkyl esters of fatty acids.

In a preferred embodiment, the reserved portion of biological material is diluted with 500 uL of heptane and then 50 uL of 0.5 N sodium methoxide in methanol solution is added. The mixture is mixed thoroughly for 30 min. at room temperature. Then, 10 uL of water is added to quench the reaction (converting sodium methoxide to methanol). After the phases separate, with the methanol/water phase on bottom and heptane phase on top, the heptane phase is separated off thereby producing the alternative, treated "Fraction 2."

Further Fractionation of the Second Aqueous Phase

In one embodiment, the second aqueous phase is split into a first portion and a second portion; the first portion is then evaporated to dryness. In an alternative embodiment, the entire second aqueous phase is evaporated to dryness. Any of the evaporation processes as described above may be used.

Production of Fraction 3

The resulting residue is then redissolved in a basic, nitrogenous organic solvent Preferably, the basic organic solvent will have a molecule weight below about 250. Examples of useful basic organic solvents include pyridine, imidazole, and aniline; preferably pyridine is used. Hydroxylamine hydrochloride is added to the selected basic organic solvent, and the resulting mixture is added to the residue to reconstitute it in a preferred embodiment one half milliliter of pyridine containing 25 milligrams per milliliter of hydroxylamine hydrochloride is added to the residue.

The basic organic solvent-hydroxylamine HCl mixture may also contain an internal standard. Useful internal standards include, but are not limited to: alkyl-substituted sugars, such as mono-hexyl- or mono-decyl-substituted sugars, trimethyl-substituted sugars, diethyl-substituted and di-propyl-substituted sugars (as sugar ethers). Other useful internal standards include those described for use with Fraction 1. A preferred internal standard is n-octyl-beta-D-glucopyranoside ("N8G"). In a preferred embodiment, 75 micrograms per milliliter of n-octyl-beta-D-glucopyranoside is used as an Internal standard.

After contacting the basic organic solvent-hydroxylamine HCl mixture (preferably containing an internal standard) with the second aqueous phase or first portion thereof, the resulting combination is allowed to stand for thirty minutes. Then, a derivatization procedure is employed to derivatize the, e.g., sugar, species in the said aqueous phase. Such derivatization procedures include silyations and others, e.g., as described in K. Blau and J. M. Halket, ads., Handbook of Derivatives for Chromatography (2d ed. 1993). Preferably a silylation procedure is used. Any silylation procedure known in the art as effective for silylating sugars may be used. Examples of such silylation procedures include those described in A. E. Pierce, Silylation of Organic Compounds (1968). A preferred silylation procedure comprises adding N,O-bis(Trimethylsilyl) trifluoroacetamide ("BSTFA") and trimethytchlorosilane ("TMCS") to said resulting combination. In a preferred embodiment, one milliliter of BSTFA (the silylating reagent) containing 1% TMCS (both obtained from Pierce Chemical Co., Rockford, Ill.) is added and allowed to react for 30 minutes to produce Fraction 3.

Production of Fraction 4 (Optional)

Where a second portion of the second aqueous phase has been reserved, this second portion is also evaporated to dryness as described above. The residue is then reconstituted by addition of either water or an aqueous solution. In a preferred embodiment a borate buffer is used. More preferably, water is used. In one embodiment, the residue is dissolved in a pH 10, 0.4 M borate buffer. Preferably at least one amino acid as internal standard is also added. In a preferred embodiment, 50 picomoles per microliter of sarcosine and norvailine are added as internal standards. The reconstituted aqueous phase is then derivatized by use of any amino add derivatization procedures as are known in the art Among the reagents useful for such derivatization are o-phthalaldehyde ("OPA"), 9-fuorenyl methyl chlorofomate ("FMOC"), fluorescamine, dansyl chloride, dabsyl chloride, 6-aminoquinolyl-N-hydroxysuccinimidyl carbarnate ("ACCQ-Tag"), and phenylisothiocyanate ("PITC"). Preferably, OPA is first added to the reconstituted aqueous phase and allowed to react, thereafter, FMOC is preferably added and allowed to react, thereby producing fraction 4.

Fraction 4 may alternatively be prepared from a portion of the original extract that has been reserved, or from a portion of the first aqueous phase.

Chromatograghy

Reconstituted Fraction 1 is preferably analyzed by capillary gas chromatography. In a preferred embodiment, the gas chromatograph is equipped with an auto-sampler, a quartz wool packed quartz inlet tube under separate temperature and pneumatics control and a CP-SIL-8CB (DB-5) 50 meter long, 0.32 millimeter internal diameter, capillary column having a stationary phase thickness of 0.25 micrometer of 5% phenyl-95% dimethylpolysiloxene (Chrompack Intemational, BV, a division of Varian U.S.A., Walnut Creek. Calif.). A solvent venting injection of 10 microliters is made at an initial column temperature of 50 degrees Centigrade, a final column temperature of 340 degrees Centigrade after 5.5 minutes and a total analysis time of 18 minutes followed by a 10 minute cool down in preparation for the next injection. The initial column Inlet carrier gas pressure is 15 psi with a final pressure of 50 psi after 13 minutes. The flame ionization detector is heated at 350 degrees Centigrade.

Treated, reconstituted Fraction 2 and/or alternative reconstituted Fraction 2 are also preferably analyzed by capillary gas chromatography. In a preferred embodiment, the gas chromatograph is equipped with an auto-sampler, a quartz wool packed quartz inlet tube under separate temperature and pneumatics control and a CP-SIL-8CB (DB-5) 50 meter long, 0.32 millimeter internal diameter, capillary column having a stationary phase thickness of 0.25 micrometer of 5% phenyl-95% dimethylpolysiloxane (Chrompack International, BV, a division of Varian U.S.A., Walnut Creek, Calif.). A solvent venting injection of 2.5 microliters is made at an initial column temperature of 50 degrees Centigrade, a final column temperature of 340 degrees Centigrade after 5.5 minutes and a total analysis time of 18 minutes followed by a 10 minute cool down in preparation for the next injection. The initial column inlet carrier gas pressure is 15 psi with a final pressure of 50 psi after 13 minutes. The flame ionization detector is heated at 350 degrees Centigrade.

Fraction 3 is also preferably analyzed by capillary gas chromatography using the same type of system as is used to chromatograph fraction 2. Optionally, Fraction 3 may be diluted with Freon 112 to reduce silica fouling of the detector; where dilution is used, a 1:1 dilution ratio is sufficient Fraction 4 is analyzed using a Hewlett Packard AMINO-QUANT Series II brand amino acid analyzer equipped with an auto-sampler.

A variety of preferred embodiments of the above-described extraction/fraction/chromatography methods are illustrated in FIGS. 3, 4, and 5. These procedures were employed in the Examples described below.

The chromatograms generated by application of the method of the present invention are then compared to identify outlier peaks. The chemical identity of outlier peaks may then be determined by use of chemical analysis methods, including but not limited to wet chemistry, comparison with standards run under the same chromatographic conditions, and GC-MS.

EXAMPLES

Example 1

Dicot Analyses

Samples of tissue taken from plants of the following tobacco varieties were obtained for testing:

Nicotiana tabacum, cultivar Burley; and

Nicotiana tabacum, cultivar Xanthi.

The method as illustrated in FIG. 3 was used to extract, fractionate, and chromatograph 4–6-leaf stage tobacco plant cuttings that included between 2 and 6 leaves, with stem. This method was used to determine chemically related differences between genetically modified and unmodified Burley tobacco plants and between genetically modified and unmodified Xanthi tobacco plants. The subject and control plants had been infected, respectively, with an exogenous gene-containing tobacco mosaic virus (TMV), and with a "functionless null insert" TMV (or none at all).

As shown in FIGS. 6A–6D and 7A–7D, Fraction 1 analysis shows an outlier peak eluting at about 11.3 minutes. Gas chromatography/mass spectroscopy of the peak eluting at about 11.3 minutes indicates that the peak is squalene. Fraction 2 analysis shows an outlier peak eluting at about 9.1 minutes. Gas chromatography/mass spectroscopy of the peak eluting at about 9.1 minutes indicates that the peak is methyl oleate. Fraction 3 analysis identified no outlier peaks. Fraction 4 analysis indicates that the sample from the genetically modified material shows significantly lower levels of aspartic acid and proline but significantly higher levels of isoleucine and leucine.

The Xanthi chromatograms did not appear to contain any significant outlier peaks (data not shown).

Example 2

Monocot Analyses

Samples of seeds of the following five corn varieties were obtained for testing:

Zea mays, Xtra-Sweet 82 hybrid, yellow, shrunken, sweet corn (72 days maturation) (Illinois Foundation Seed, Inc., Tolono, Ill.), labeled herein as "Illinois Sweet;"

Zea mays, POPS-RITE Premium Heart-of-the-Ear popcorn (Agrilink Foods, Rochester, N.Y.), labeled herein as "popcorn;"

Zea mays, LG 2483 hybrid, yellow, feed corn (99 days maturation) (LG Seeds, Inc., Peoria, Ill.), labeled herein as "Hybred Seed;"

Zea mays, "Bird Feed Shelled Corn" (Cohoon's Elevator, Midland, Mich.), labeled herein as "Albe Feed."

Zea mays, Radiance hybrid, bi-color, shrunken, sweet corn (73 days maturation) (Illinois Foundation Seed, Inc., Tolono, Ill.), labeled herein as "Radiance;"

The method as illustrated in FIG. 5, without producing Fraction 4, was used to extract, fractionate, and chromatograph corn seed that had been ground for 60 seconds at 20,000 RPM over a 0.5 mm pore screen, in a PULVERIZER Centrifuge/Grinding Mill (Sybron/Brinkmann instruments). This method was used to cross-compare the metabolites from these corn samples. As shown in FIG. 8A–8E, 9A–9E, and 10A–10E, the Illinois Sweet corn: Fraction 1 shows outlier peaks at about 8.2, 8.5, 8.9, 11, and 12–13 minutes; Fraction 2 shows outlier peaks at about 9.75, 10.5, and 10.6 minutes; and Fraction 3 shows outlier peaks at about 5.4 and 8–8.3 minutes.

Example 3

Fungi Analyses

Lyophilized samples of broth cultures of the following two yeasts were obtained for testing:

Candida tropicalis (Castellani) Berkhout (ATCC Accession No. 750); and

Yarrowia lipolytica (Wickerham et al.) van der Walt et von Arx (ATCC Accession No. 8661).

Figure 11A:
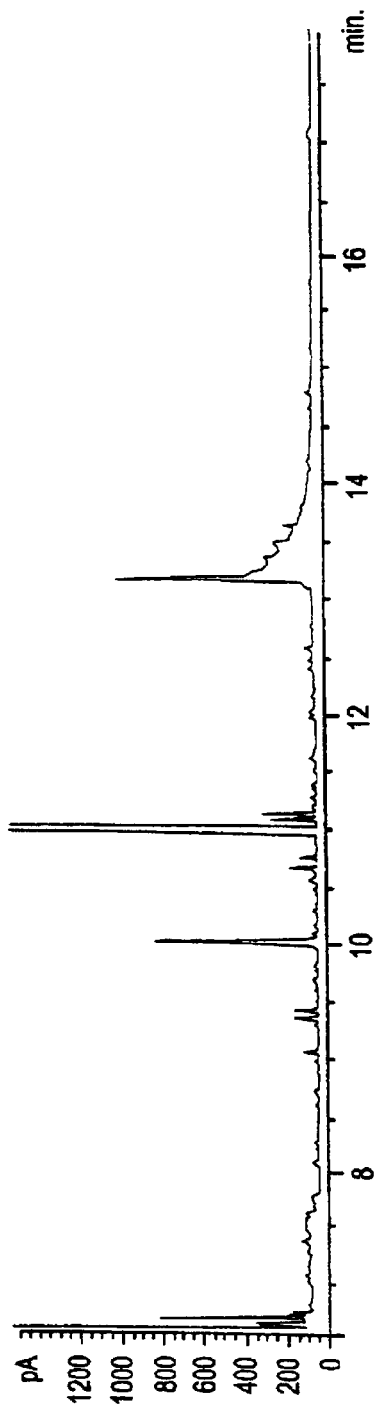
FIG. 11A shows a chromatogram of a Fraction 1 extract from *Candida tropicalis* with glucose feed.
Figure 11B:
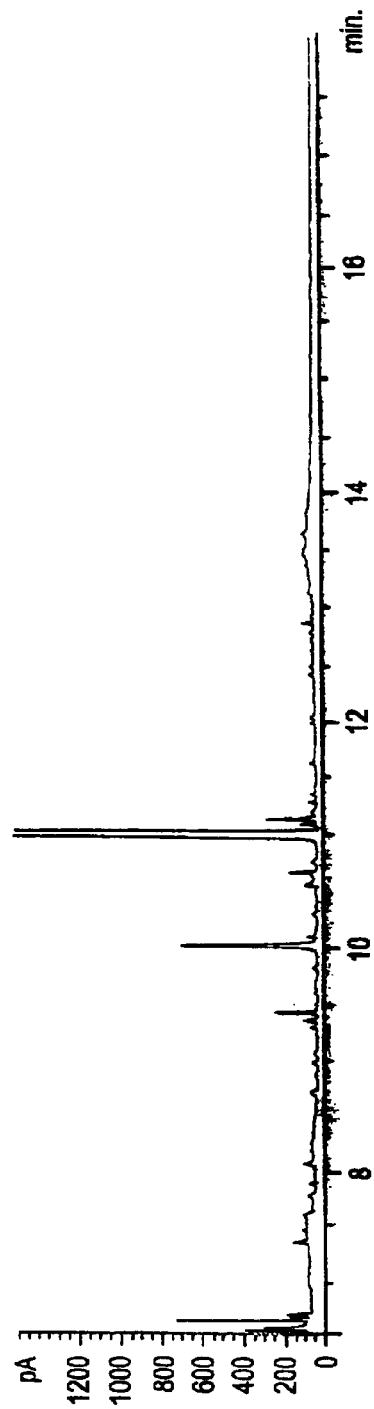
FIG. 11B shows a chromatogram of a Fraction 1 extract from *Candida tropicalis* with dodecane feed.
Figure 15A:
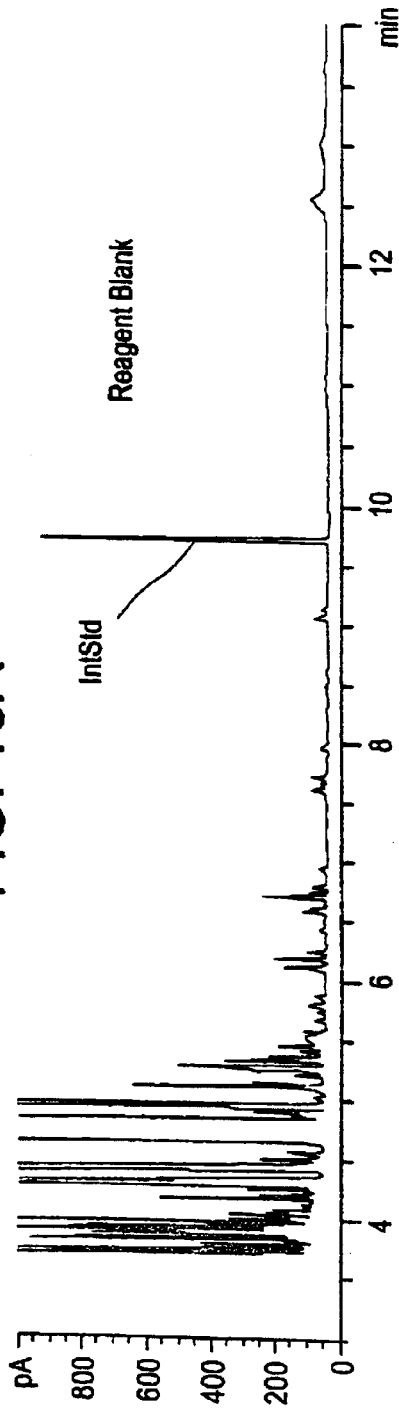
FIGS. 15A–15E show a reagent blank chromatogram (FIG. 15A) and chromatograms of Fraction 3 extracts from the yeast *Y. lipolytica* grown on glucose feed or dodecane feed (FIGS. 15B–15C) and from the yeast *C. tropicalis* grown on glucose feed or dodecane feed (FIGS. 15D–15E).
Figure 15B:
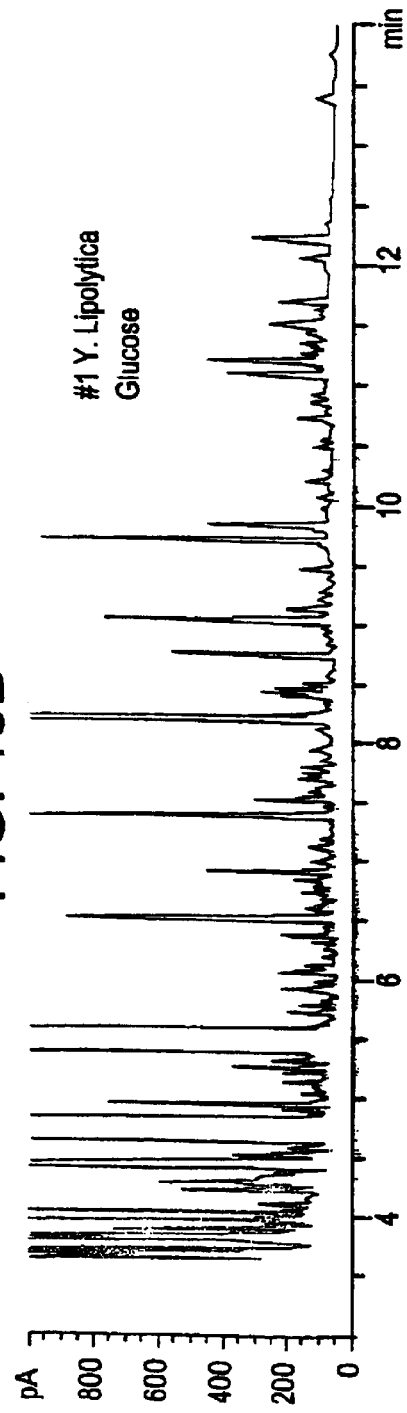
Figure 15C:
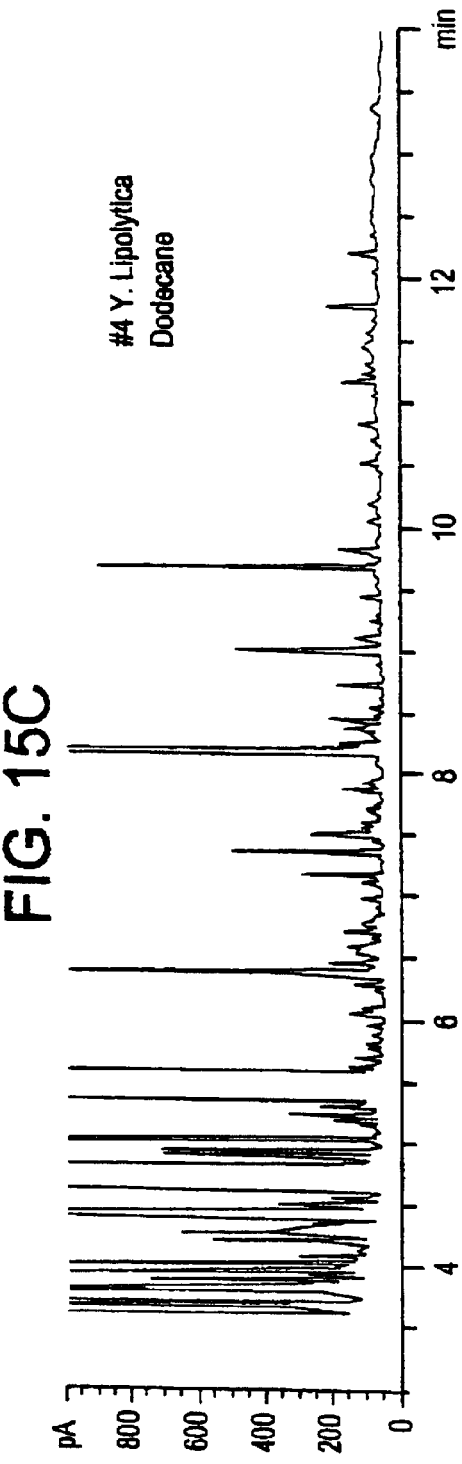
Figure 15D:
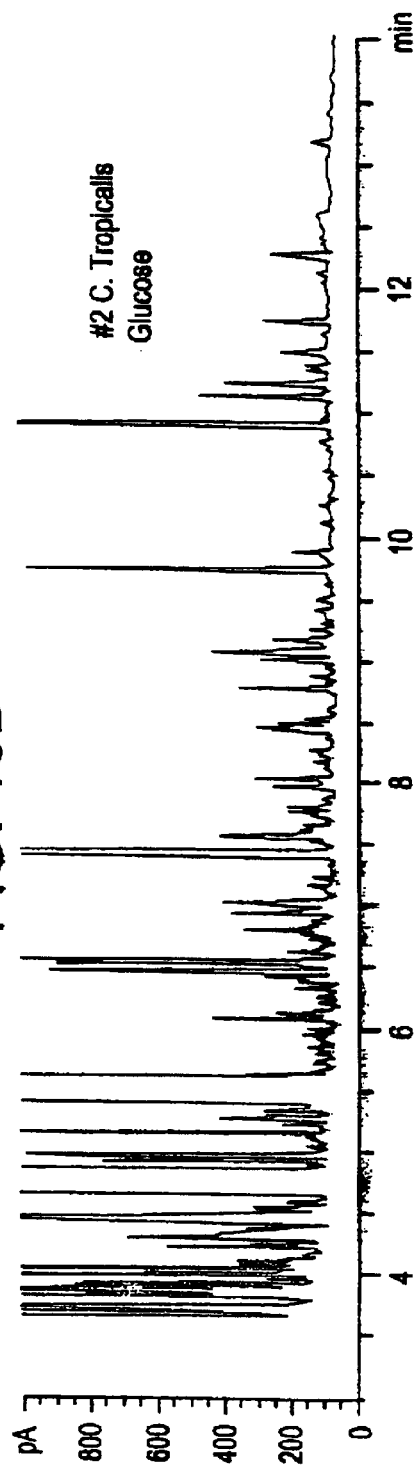
Figure 15E:
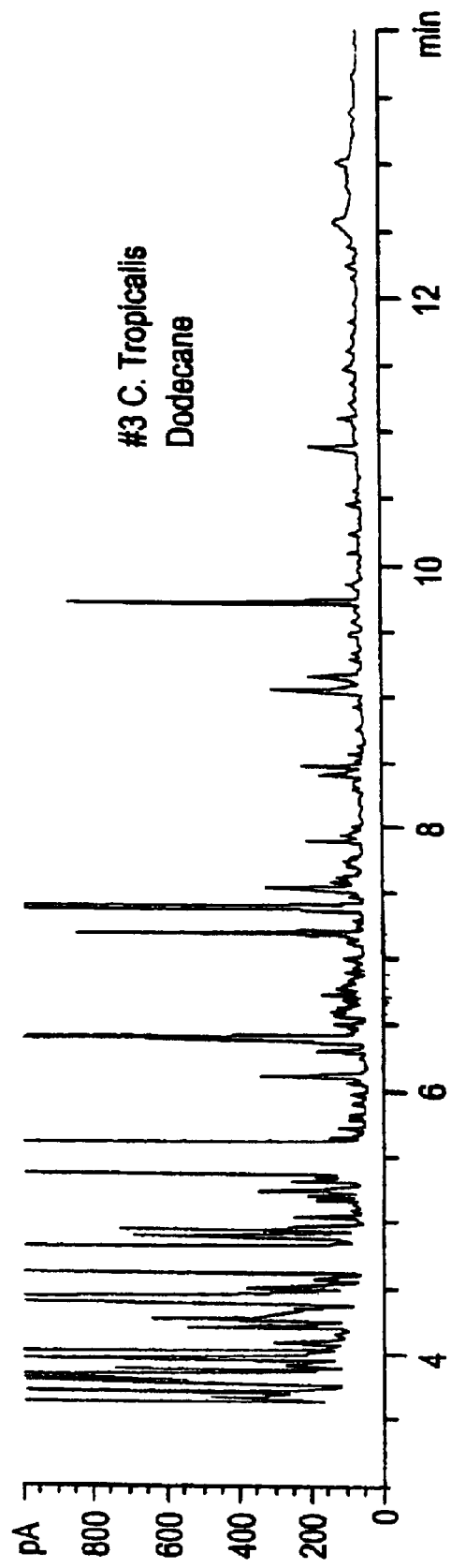

The method as illustrated in FIG. 5 (without formation of Fraction 4) was used to extract, fractionate, and chromatograph samples of the above species grown on either glucose (control) or dodecane (subject) feedstock. FIGS 1A–11B, 12A–12B, and 15D–15E show chromatograms obtained for Fraction 1, 2, and 3 analyses of C. tropicals, and FIGS. 13A–13B, 14A–14B, and 15B–15C show chromatograms obtained for Fraction 1, 2, and 3 analyses of Y. lipolytica. Many outlier peaks may be noted in FIGS. 11A–11B. 12A–12B, and 15D–15E. One outlier peak is sed at about 13.2 minutes in FIG. 13 (identified as egosterol).

Example 4

Prokaryote Analyses

Lyophilized samples of broth cultures of the following three bacteria were obtained for testng:

Pseudomonas fluorescens Migula 1895 (obtained as Accession No. NRRL B-4290 from the Agricultural Research Service (ARS) Culture Collection at the National Center for Agricultural Utilization Research [NCAUR] (formerly the Northern Regional Research Laboratory [NRRL] of the United States Department of Agriculture, 1815 N. University Street, Peoria, Ill. 61604, labeled herein as "MB101;"

Pseudomonas putida (Trevisan) Migula (ATCC Accession No. 33015), labeled herein as "MB376."

The method as illustrated in FIG. 5 (without formation of Fraction 4) was used to extract, fractionate, and chromatograph samples of the above species. Comparison of their Fraction 2 chromatograms shows numerous outlier peaks (data not shown).

One of ordinary skill in the art will recognize various other embodiments of the methods disclosed herein. These are intended to be included within the instant invention as claimed below.

What is claimed is:

1. A method for determining chemically related differences between subject biological material and control biological material, comprising the steps of:

(A) providing:

(1) at least one sample of at least one subject biological material, and (2) at least one sample of at least one control biological material;

(B) optionally reserving at least one portion of each said sample of biological material, thereby producing a reserved portion of, and leaving a remainder sample of, each said, sample of biological material;

(C) extracting each said sample or remainder sample of biological material with a fluid extractant, said extractant comprising
  (1) an aqueous isopropanol-KOH mixture, or
  (2) aqueous isopropanol,
thereby producing an original extract of each said sample or remainder sample of biological material;

(D) optionally splitting each said original extract into a first portion and a second portion;

(E) preparing a set of reconstituted first fractions and a set of first aqueous phases by
  (1) adding to, and mixing with, each said original extract, or with each said first portion thereof, a non-polar organic solvent,
  (2) allowing said organic solvent and said original extract to coalesce to form a first organic phase and a first aqueous phase,
  (3) separating said first organic phase from said first aqueous phase, each said separated first organic phase then being a first fraction, and each said separated first aqueous phase being a member in said set of first aqueous phases,
  (4) evaporating to dryness each said first fraction, thereby producing a first fraction residue, and
  (5) reconstituting said first fraction by adding to, and mixing with, said first fraction residue, a non-polar organic solvent to produce a reconstituted first fraction, each of said reconstituted first fractions being a member in said set of reconstituted first fractions;

(F) optionally splitting each said first aqueous phase into a first portion and a second portion;

(G) preparing at least one set of esterified second fractions and, optionally, a set of second aqueous phases, by either
  (1) performing
    (a) a fractionation technique comprising the steps of
      (i) acidifying each said first aqueous phase to a pH below pH6, to form an acidified first aqueous phase,
      (ii) adding to, and mixing with, each said acidified first aqueous phase, a non-polar organic solvent,
      (iii) allowing said organic solvent and said acidified first aqueous phase to coalesce to form a second organic phase and a second aqueous phase,
      (iv) separating said second organic phase from said second aqueous phase, each said separated second organic phase then being a second fraction, and each said separated second aqueous phase being a member in said set of second aqueous phases; and
    (b) a reconstitution technique comprising the steps of
      (i) evaporating to dryness each said second fraction, thereby producing a second fraction residue, and
      (ii) reconstituting said second fraction by adding to, and mixing with, said second fraction residue, a non-polar organic solvent to produce a reconstituted second fraction; and
    (c) a methylation of said reconstituted second fraction,
thereby producing an esterified second fraction, each said esterified second fraction being a member in said set of esterified second fractions; and/or
  (2) performing a combined extraction/esterification technique comprising the steps of
    (a) adding to each said reserved portion of biological material, a C5–C8 aliphatic solvent, to form a diluted portion,
    (b) adding to, and mixing with, said diluted portion a C1–C3 alcohol and a corresponding, metal C1–C3 alkoxide, to form an esterified mixture, and
    (c) adding to, and mixing with, said esterified mixture, water
    (d) allowing said aliphatic solvent to coalesce to form a second organic phase, distinct from the remainder of said mixture, and
    (e) separating said second organic phase from said remainder,
thereby producing an esterified second fraction, each said esterified second fraction being a member in said set of esterified second fractions;

(H) optionally splitting each said second aqueous phase into a first portion and a second portion;

(I) preparing a set of silylated third fractions by performing
  (1) a reconstitution technique comprising the steps of
    (a) evaporating to dryness,
      (i) each said first aqueous phase, or each said first portion thereof, in the event step (G)(1) is not performed, or
      (ii) each said second aqueous phase, or each said first portion thereof, in the event step (G)(1) is performed, thereby producing a first aqueous phase residue, and
    (b) reconstituting said first aqueous phase by adding to, and mixing with, said first aqueous phase residue, a basic nitrogenous organic solvent to produce a reconstituted first aqueous phase; and
  (2) a derivatization technique comprising adding to, and reacting with, said reconstituted first aqueous phase, hydroxylamine to form a derivatized first aqueous phase; and
  (3) a silylating technique on each said derivatized first aqueous phase,
thereby producing a silylated third fraction, each said silylated third fraction being a member in the set of silylated third fractions;

(J) optionally preparing a set of fourth fractions by
  (1) evaporating to dryness:
    (a) each said second portion of said original extract; or
    (b) either one of
      (i) each said second portion of said first aqueous phase, in the event step (G)(1) is not performed, or
      (ii) each said second portion of said second aqueous phase, in the event step (G)(1) is performed; or
    (c) both (a) and (b), thereby producing at least one second aqueous phase residue, and
  (2) reconstituting each said second aqueous phase residue by adding to, and mixing with, said second aqueous phase residue, an aqueous liquid to produce a fourth fraction, each said fourth fraction being a member in the set of fourth fractions;

(K) analyzing each of said first fractions, esterified second fractions, silylated third fractions, and optionally said fourth fractions, to produce at least one set of subject chromatograms and at least one set of control chromatograms, each set representing an analysis of one sample of biological material; and (L) comparing said subject chromatograms with said control chromatograms to identify outlier peaks representing chemically related differences between said subject biological material and said control biological material.

2. The method according to claim 1, further comprising, after step (L), the step: (M) determining the chemical identity of at least one outlier peak.

3. The method according to claim 1, wherein in step (C), said fluid extractant comprises (1) a mixture of KOH and an aqueous solution of about 10–90% isopropanol, or (2) an aqueous solution of about 10–90% isopropanol.

4. The method according to claim 3, wherein said aqueous solution is about 25–75% isopropanol.

5. The method according to claim 4, wherein said aqueous solution is about 50% isopropanol.

6. The method according to claim 5, wherein said aqueous solution is about 70% isopropanol.

7. The method according to claim 3, wherein said mixture comprises about 0.01–0.5N KOH.

8. The method according to claim 7, wherein said mixture comprises about 0.1 N KOH.

9. The method according to claim 1, wherein in step (L) at least one of said control chromatograms is an average or model chromatogram, or at least one of said subject chromatograms is an average or model chromatogram, or at least one of each of said chromatograms is an average or model chromatogram.

* * * * *